United States Patent
Koolen et al.

(10) Patent No.: US 9,158,194 B2
(45) Date of Patent: Oct. 13, 2015

(54) METROLOGY METHOD AND APPARATUS, AND DEVICE MANUFACTURING METHOD

(71) Applicant: ASML Netherlands B.V., Veldhoven (NL)

(72) Inventors: Armand Eugene Albert Koolen, Nuth (NL); Henricus Petrus Maria Pellemans, Veldhoven (NL); Maurits Van Der Schaar, Eindhoven (NL); Peter Clement Paul Vanoppen, Hechtel-Eksel (BE); Michael Kubis, Düsseldorf (DE)

(73) Assignee: ASML Netherlands B.V., Veldhoven (NL)

( * ) Notice: Subject to any disclaimer, the term of this patent is extended or adjusted under 35 U.S.C. 154(b) by 501 days.

(21) Appl. No.: 13/628,697

(22) Filed: Sep. 27, 2012

(65) Prior Publication Data
US 2013/0100427 A1    Apr. 25, 2013

Related U.S. Application Data

(60) Provisional application No. 61/550,615, filed on Oct. 24, 2011.

(51) Int. Cl.
G01B 11/00    (2006.01)
G01B 11/14    (2006.01)
(Continued)

(52) U.S. Cl.
CPC .. *G03F 1/42* (2013.01); *G01B 9/04* (2013.01); *G01N 21/47* (2013.01);
(Continued)

(58) Field of Classification Search
CPC ..... G01B 9/04; G01N 21/47; G01N 21/4788;
G01N 21/9501; G01N 21/956; G03F 1/42;
G03F 7/70616; G03F 7/70633; G03F 7/70666;
G03F 7/70675; G03F 9/70–9/7019; G03F
9/7069; G03F 9/7088; G03F 9/7092
USPC .................. 355/67, 68, 71, 77; 356/399–401,
356/614–616; 430/22, 30
See application file for complete search history.

(56) References Cited

U.S. PATENT DOCUMENTS

2006/0232777 A1    10/2006  Finarov et al.
2011/0043791 A1     2/2011  Smilde et al.
(Continued)

FOREIGN PATENT DOCUMENTS

WO    WO 2009/078708 A1    6/2009
WO    WO 2009/106279 A1    9/2009
(Continued)

*Primary Examiner* — Colin Kreutzer
(74) *Attorney, Agent, or Firm* — Sterne, Kessler, Goldstein & Fox P.L.L.C.

(57) ABSTRACT

An approach is used to estimate and correct the overlay variation as function of offset for each measurement. A target formed on a substrate includes periodic gratings. The substrate is illuminated with a circular spot on the substrate with a size larger than each grating. Radiation scattered by each grating is detected in a dark-field scatterometer to obtain measurement signals. The measurement signals are used to calculate overlay. The dependence (slope) of the overlay as a function of position in the illumination spot is determined. An estimated value of the overlay at a nominal position such as the illumination spot's center can be calculated, correcting for variation in the overlay as a function of the target's position in the illumination spot. This compensates for the effect of the position error in the wafer stage movement, and the resulting non-centered position of the target in the illumination spot.

16 Claims, 12 Drawing Sheets

(51) Int. Cl.

| | |
|---|---|
| G03B 27/32 | (2006.01) |
| G03B 27/54 | (2006.01) |
| G03B 27/72 | (2006.01) |
| G03B 27/74 | (2006.01) |
| G03C 5/00 | (2006.01) |
| G03F 1/42 | (2012.01) |
| G03F 7/20 | (2006.01) |
| G03F 9/00 | (2006.01) |
| G01N 21/47 | (2006.01) |
| G01B 9/04 | (2006.01) |

(52) U.S. Cl.
CPC ....... *G03F 7/70616* (2013.01); *G03F 7/70633* (2013.01); *G03F 9/70* (2013.01); *G03F 9/7069* (2013.01); *G03F 9/7088* (2013.01)

(56) References Cited

U.S. PATENT DOCUMENTS

2012/0113404 A1   5/2012   Hsu et al.
2012/0123581 A1   5/2012   Smilde et al.

FOREIGN PATENT DOCUMENTS

| WO | WO 2011/012624 A1 | 2/2011 |
| WO | WO 2011/023517 A1 | 3/2011 |
| WO | WO 2012/062501 A1 | 5/2012 |

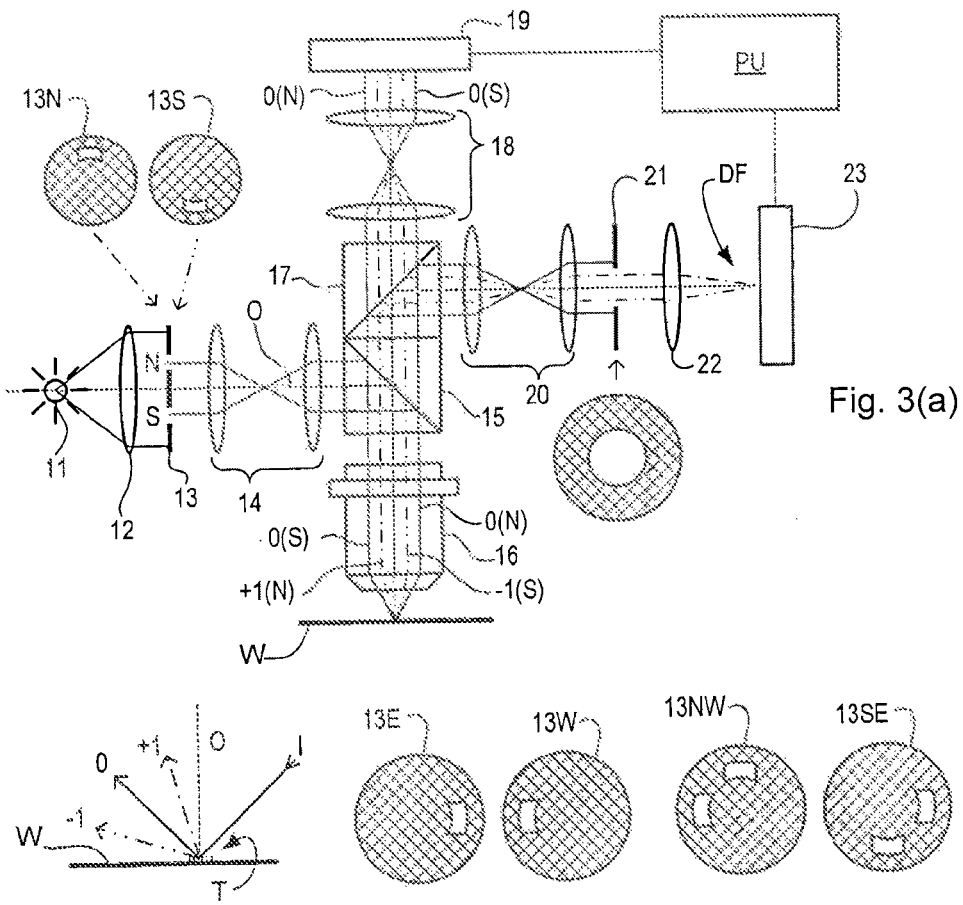
Fig. 3(a)
Fig. 3(b)  Fig. 3(c)  Fig. 3(d)
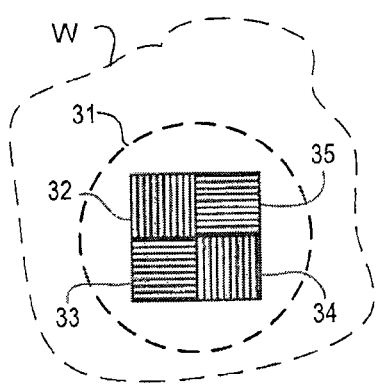
Fig. 4
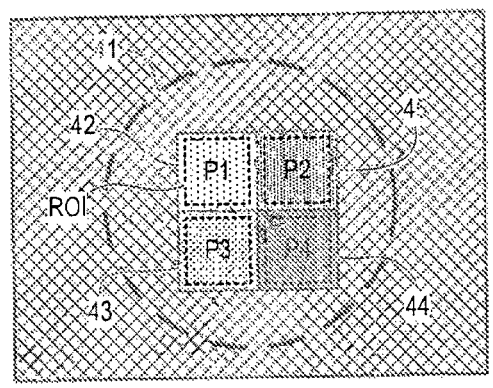
Fig. 5

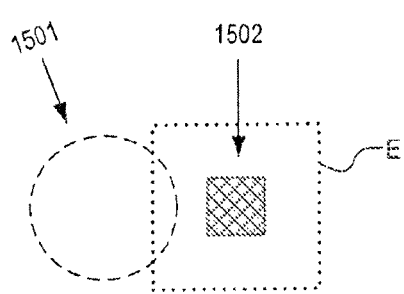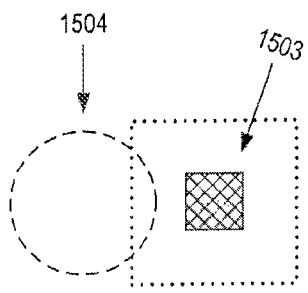
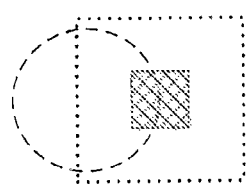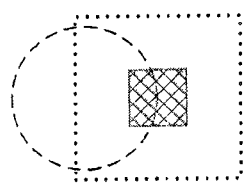
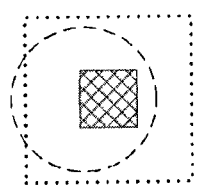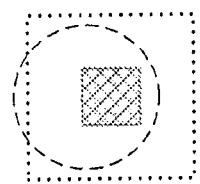
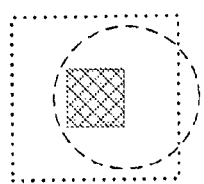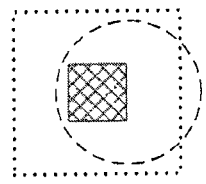
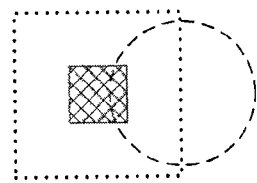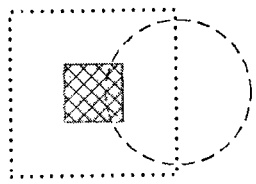
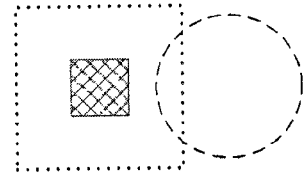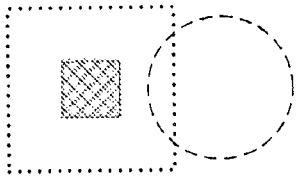
Fig. 15a               Fig. 15b

METROLOGY METHOD AND APPARATUS, AND DEVICE MANUFACTURING METHOD

BACKGROUND

1. Field of the Present Invention

The present invention relates to methods and apparatus for measuring a property of at target, such as overlay, usable, for example, in the manufacture of devices by lithographic techniques and to methods of manufacturing devices using lithographic techniques.

2. Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

The targets used by conventional scatterometers are relatively large, e.g., 40 µm by 40 µm, gratings and the measurement beam generates a spot that is smaller than the grating (i.e., the grating is underfilled). This simplifies mathematical reconstruction of the target as it can be regarded as infinite. However, in order to reduce the size of the targets, e.g., to 10 µm by 10 µm or less, e.g., so they can be positioned in amongst product features, rather than in the scribe lane, metrology has been proposed in which the grating is made smaller than the measurement spot (i.e., the grating is overfilled). Typically such targets are measured using dark field scatterometry in which the zeroth order of diffraction (corresponding to a specular reflection) is blocked, and only higher orders processed. Examples of dark field metrology can be found in international patent applications WO 2009/078708 and WO 2009/106279 which documents are hereby incorporated by reference in their entirety. Further developments of the technique have been described in patent publications WO 2011/012624 and WO 2011/023517 and WO 2012/062501. The contents of all these applications are also incorporated herein by reference in their entireties. Diffraction-based overlay (DBO) using dark-field detection of the diffraction orders enables overlay measurements on smaller targets. These targets can be smaller than the illumination spot and may be surrounded by product structures on a wafer. Multiple targets can be measured in one image.

In the known dark-field metrology technique, overlay measurement results are obtained by measuring the target twice under certain conditions, while either rotating the target or changing the illumination mode or imaging mode to obtain separately the $-1^{st}$ and the $+1^{st}$ diffraction order intensities.

In the special case when an overfilled target is located in an environment that is empty of features, such as a non-reflective background, then, instead of dark-field metrology, angularly-resolved metrology can be used to measure the target to obtain separately the $-1^{st}$ and the $+1^{st}$ diffraction order intensities at the same time in the pupil plane of the inspection apparatus. In this case the intensity measured in the pupil plane is not contaminated by light scattered from the environment around the target.

It is known that in scatterometers, wafer stage positioning error is such that a target can incur a random position error (for example +/−3 µm) with respect to the measurement spot center in each wafer stage movement. This means that the target grating will not always be centered with respect to the measurement spot. The measured overlay has been found to vary from the value measured with the target at the center of the measurement spot. This overlay measurement error has been found to be linear (at least in part) and anti-symmetric with respect to displacement from the center of the illumination spot, as discussed below in relation to FIGS. 7 and 11. Therefore, when performing overlay measurements, in order to minimize overlay measurement error the target grating should be centered with respect to the illumination spot. If the target is not centered, then the overlay measurement will have systematic errors introduced. For composite targets with multiple grating orientations and/or overlay biases, it is not possible to have all the gratings centered in the illumination spot simultaneously.

SUMMARY

It is desirable to provide a method and apparatus for measuring a property of a target using periodic structures, in which for example the effect of composite targets and stage positioning errors leading to non-centered targets in the measurement spot are mitigated.

The present invention in a first aspect provides a method of determining a property of a target comprising at least one periodic structure, the target formed by a lithographic process on a substrate, the method including illuminating the substrate with a beam of radiation, having an illumination region on the substrate with a size larger than at least one periodic structure of the target, detecting radiation scattered by the at least one periodic structure at a plurality of positions in the illumination region, and calculating a value of the property of the target corresponding to a nominal position of the at least one periodic structure in the illumination region when the radiation was detected, by using the detected radiation and correcting for variation of the property as a function of the at least one periodic structure's position in the illumination region.

The present invention in a second aspect provides a method of determining a property of a target comprising at least one periodic structure, the target formed by a lithographic process on a substrate, the method including illuminating the substrate with a beam of radiation, having an illumination region on the substrate with a size larger than at least one periodic structure of the target, detecting radiation scattered by the at least one periodic structure at a plurality of positions in the illumination region, calculating a value of the property of the target corresponding to a nominal position of the at least one periodic structure in the illumination region when the radiation was detected, by using the detected radiation and correcting for variation of the property as a function of the at least one periodic structure's position in the illumination region, determining a dependence of a scattering property obtained from the detected radiation as a function of position in the illumination region, and determining the position offset of at least one of the at least one periodic structure, wherein the calculating includes using the determined dependence and the determined position offset.

The present invention in a third aspect provides a method of determining a property of a target comprising at least one periodic structure, the target formed by a lithographic process on a substrate, the method including illuminating the substrate with a beam of radiation, having an illumination region on the substrate with a size larger than at least one periodic structure of the target, detecting radiation scattered by the at least one periodic structure at a plurality of positions in the illumination region, and calculating a value of the property of the target corresponding to a nominal position of the at least one periodic structure in the illumination region when the radiation was detected, by using the detected radiation and correcting for variation of the property as a function of the at least one periodic structure's position in the illumination region, the detecting is performed while at least one of the illumination region and the target are moved relative to each other along a path with the at least one periodic structure passing fully through the illumination region, and the method further includes integrating at least one measurement signal along the path and step (c) includes using the at least one integrated measurement signal.

The present invention in a fourth aspect provides an inspection apparatus configured for determining a property of a target comprising at least one periodic structure, the target formed by a lithographic process on a substrate, the inspection apparatus comprising: an illumination arrangement operable to illuminate the substrate with a beam of radiation, having an illumination region on the substrate with a size larger than at least one periodic structure of the target, a detection arrangement operable to detect radiation scattered by the at least one periodic structure at a plurality of positions in the illumination region, and a computational arrangement operable to calculate a value of the property of the target corresponding to a nominal position of the at least one periodic structure in the illumination region when the radiation was detected, by using the detected radiation and correcting for variation of the property as a function of the at least one periodic structure's position in the illumination region.

The present invention in a fifth aspect provides an inspection apparatus configured for determining a property of a target comprising at least one periodic structure, the target formed by a lithographic process on a substrate, the inspection apparatus comprising: an illumination arrangement operable to illuminate the substrate with a beam of radiation, having an illumination region on the substrate with a size larger than at least one periodic structure of the target, a detection arrangement operable to detect radiation scattered by the at least one periodic structure at a plurality of positions in the illumination region, and a computational arrangement operable to: determine a dependence of a scattering property obtained from the detected radiation as a function of position in the illumination region, determine the position offset of at least one of at least one the periodic structure, and calculate a value of the property of the target corresponding to a nominal position of the at least one periodic structure in the illumination region when the radiation was detected, by using the detected radiation and correcting for variation of the property as a function of the at least one periodic structure's position in the illumination region using the determined dependence and the determined position offset.

The present invention in a sixth aspect provides an inspection apparatus configured for determining a property of a target comprising at least one periodic structure, the target formed by a lithographic process on a substrate, the inspection apparatus comprising: an illumination arrangement operable to illuminate the substrate with a beam of radiation, having an illumination region on the substrate with a size larger than at least one periodic structure of the target, a detection arrangement operable to detect radiation scattered by the at least one periodic structure at a plurality of positions in the illumination region, and a computational arrangement operable to calculate a value of the property of the target corresponding to a nominal position of the at least one periodic structure in the illumination region when the radiation was detected, by using the detected radiation and correcting for variation of the property as a function of the at least one periodic structure's position in the illumination region. a movement arrangement operable to move at least one of the illumination region and the target relative to each other, and wherein: the detection arrangement is further operable to detect radiation while at least one of the illumination region and the target are moved relative to each other along a path with the at least one periodic structure passing fully through the illumination region, and the computational arrangement is further operable to integrate at least one measurement signal along the path and to calculate the value of the property of the target using the at least one integrated measurement signal.

The present invention in a seventh aspect provides a lithographic system comprising: a lithographic apparatus comprising: an illumination optical system arranged to illuminate a pattern, a projection optical system arranged to project an image of the pattern onto a substrate, and an inspection apparatus according to the fourth aspect as set forth above, or according to the fifth aspect as set forth above, or according to the sixth aspect as set forth above, wherein the lithographic apparatus is arranged to use the determined property from the inspection apparatus in applying the pattern to further substrates.

The present invention in an eighth aspect provides a method of manufacturing devices wherein a device pattern is applied to a series of substrates using a lithographic process, the method including inspecting at least one target comprising at least one periodic structure formed as part of or beside the device pattern on at least one of the substrates using an inspection method according to the first aspect as set forth above, or according to the second aspect as set forth above, or according to the third aspect as set forth above, and controlling the lithographic process for later substrates in accordance with the result of the inspection method.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

FIG. 3a-3d comprises (a) a schematic diagram of a dark field scatterometer for use in measuring targets according to embodiments of the present invention using a first pair of illumination apertures, (b) a detail of diffraction spectrum of a target grating for a given direction of illumination (c) a second pair of illumination apertures providing further illumination modes in using the scatterometer for diffraction based overlay measurements and (d) a third pair of illumination apertures combining the first and second pair of apertures.

FIG. 4 depicts a known form of multiple grating target and an outline of a measurement spot on a substrate.

FIG. 5 depicts an image of the target of FIG. 4 obtained in the scatterometer of FIG. 3.

Figure 6:
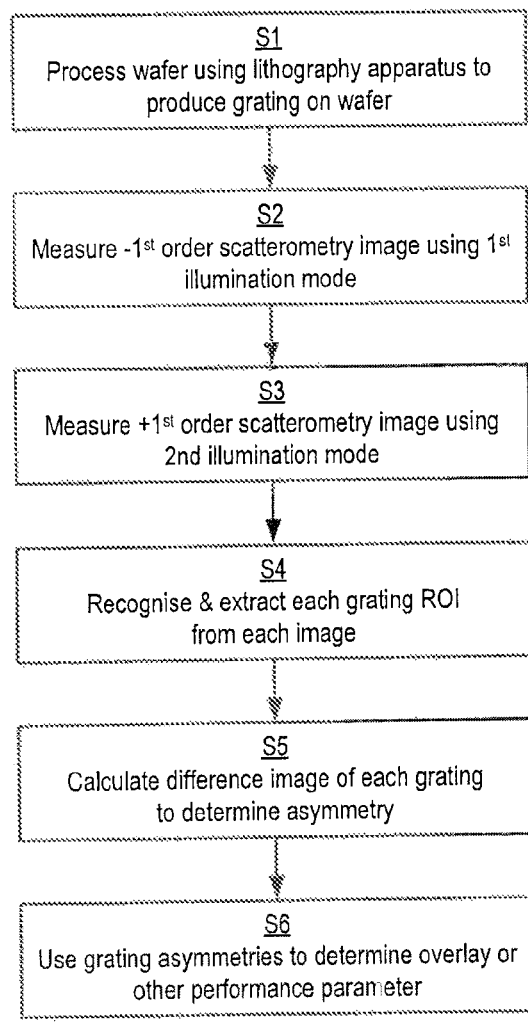

FIG. 6 is a flowchart showing the steps of an overlay measurement using the scatterometer of FIG. 3.

Figure 7:
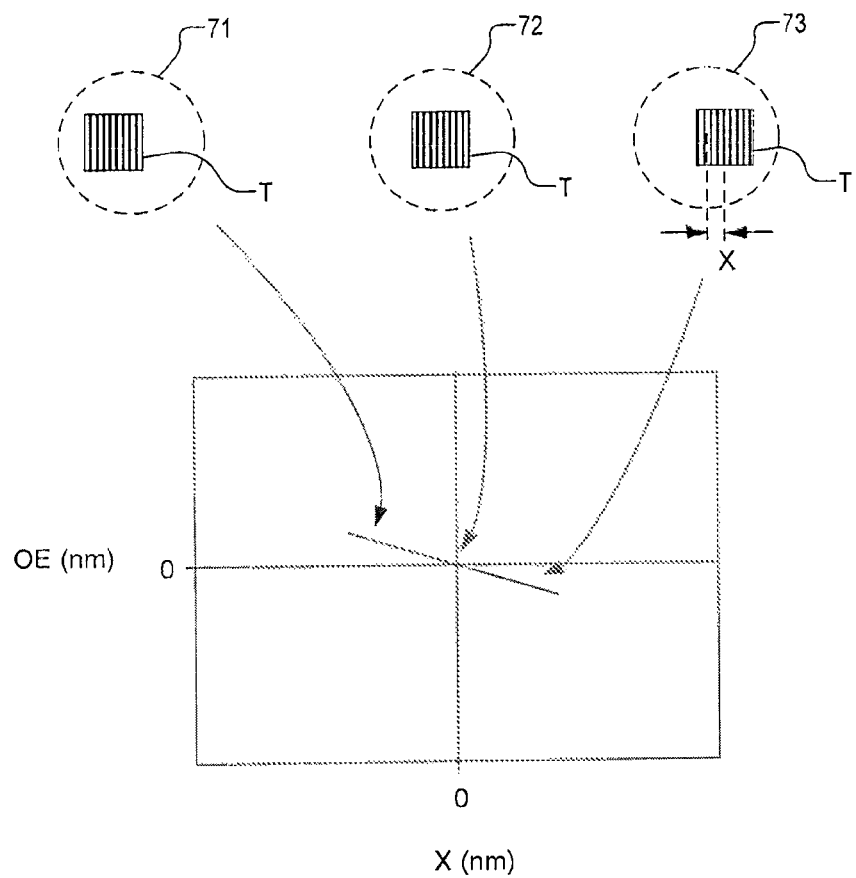

FIG. 7 is a graph showing overlay measurement error as a linear function of position of the target with respect to the illumination spot.

FIGS. 8a to 8d illustrate an illumination spot with a target with multiple gratings in different positions.

Figure 9:
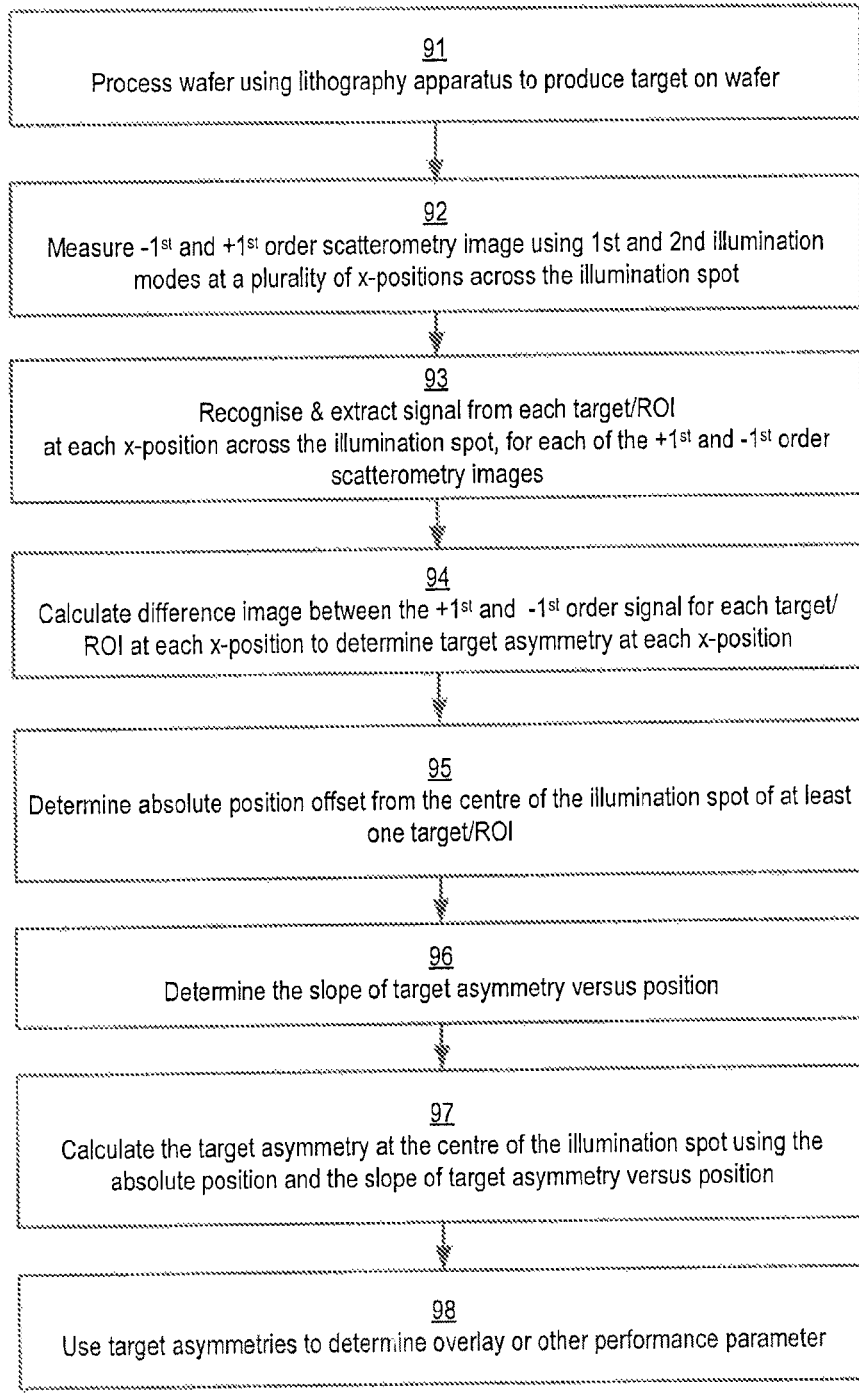

FIG. 9 illustrates a method according to an embodiment of the present invention using dark-field diffraction-based overlay measurements.

Figure 10:
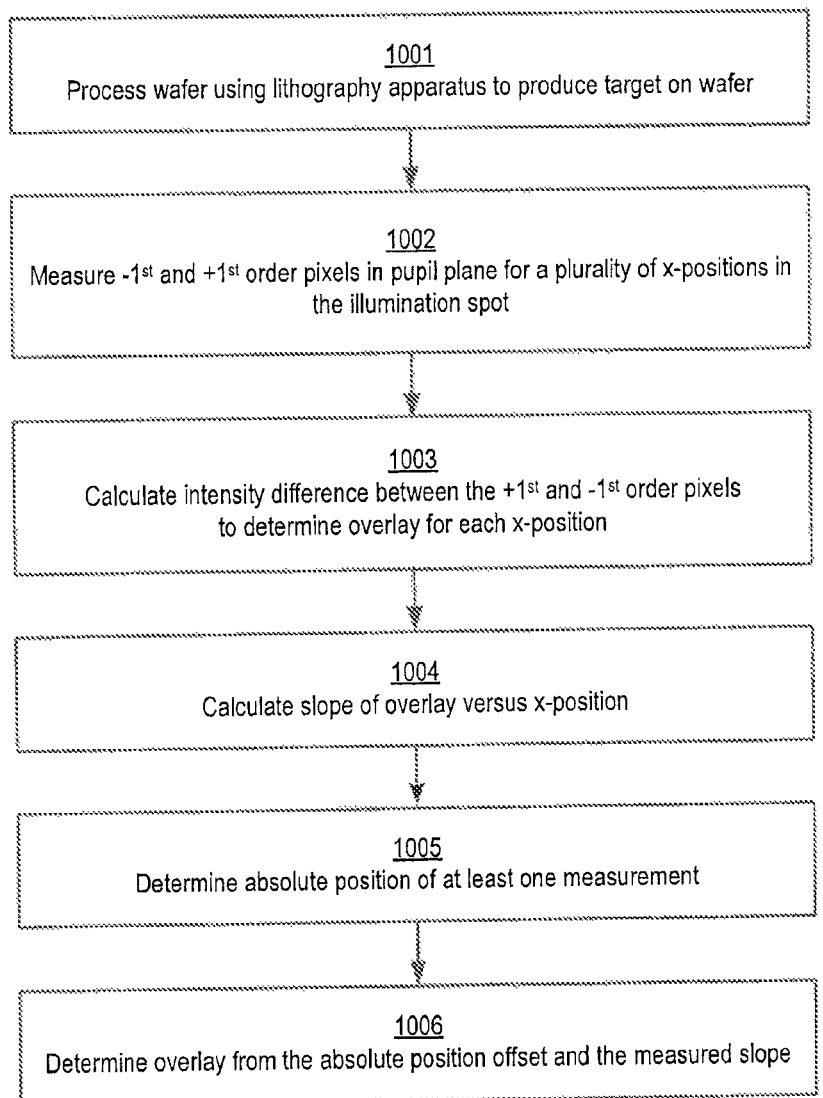

FIG. 10 illustrates a method according to an embodiment of the present invention using an angularly resolved scatterometer overlay measurement.

Figure 11:
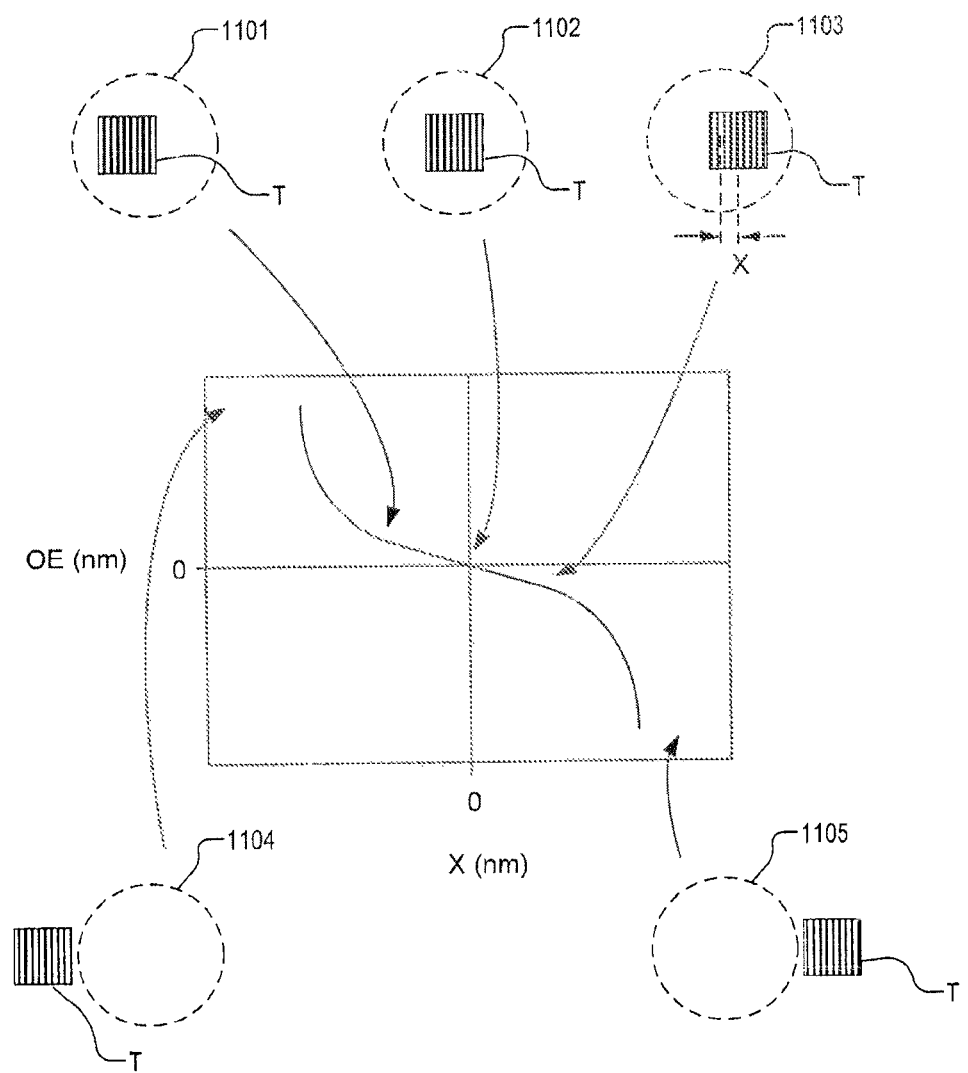

FIG. 11 is a graph showing overlay measurement error as an anti-symmetric function of position of the target with respect to the illumination spot.

Figure 12A:
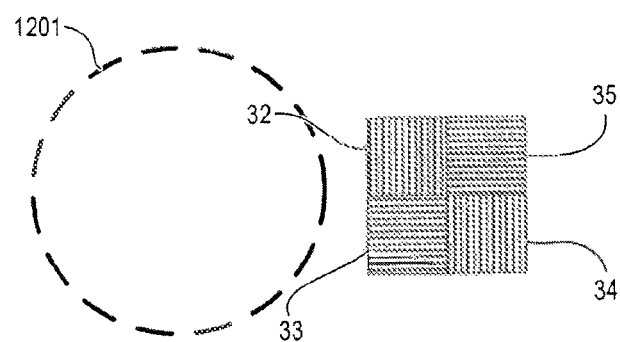
Figure 12B:
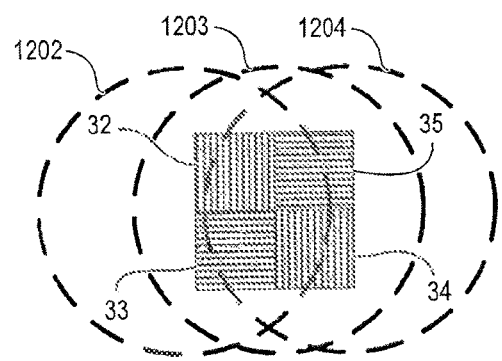
Figure 12C:
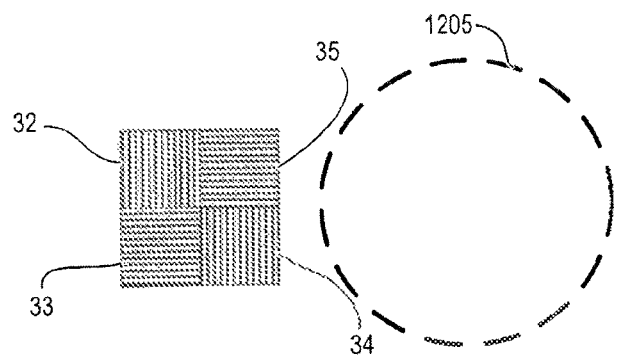

FIGS. 12a to 12c illustrate an illumination spot being scanned across a target with multiple gratings.

Figure 13:
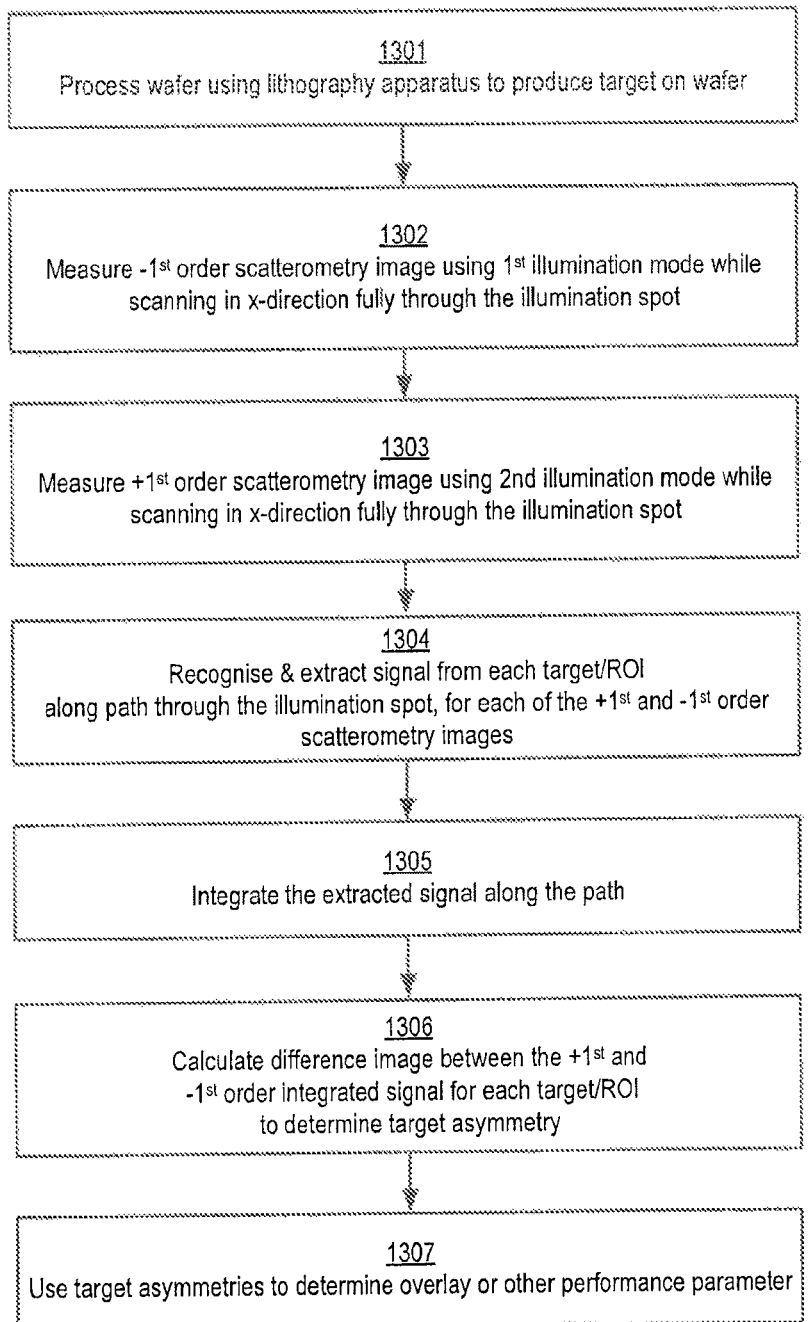

FIG. 13 illustrates a method according to an embodiment of the present invention using dark-field diffraction-based overlay measurements.

Figure 14:
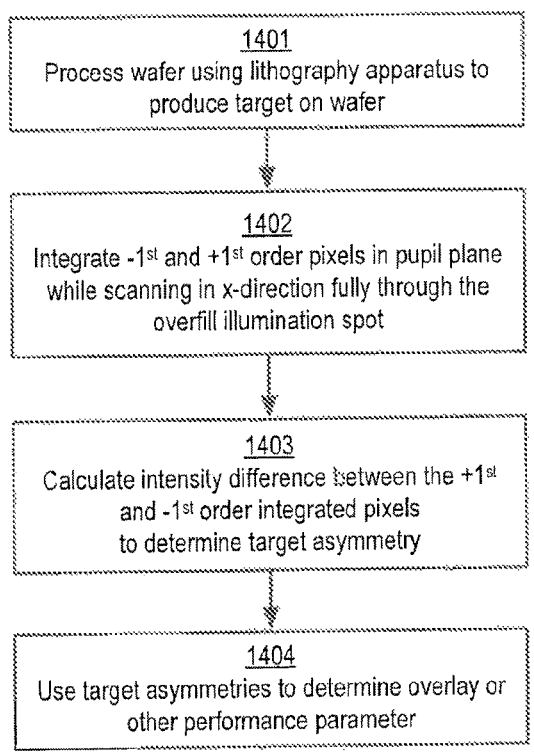

FIG. 14 illustrates a method according to an embodiment of the present invention using an angularly resolved scatterometer overlay measurement. and FIGS. 15a and 15b respectively illustrate scanning an illumination spot across a target and conversely scanning a target across an illumination spot.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Figure 1:
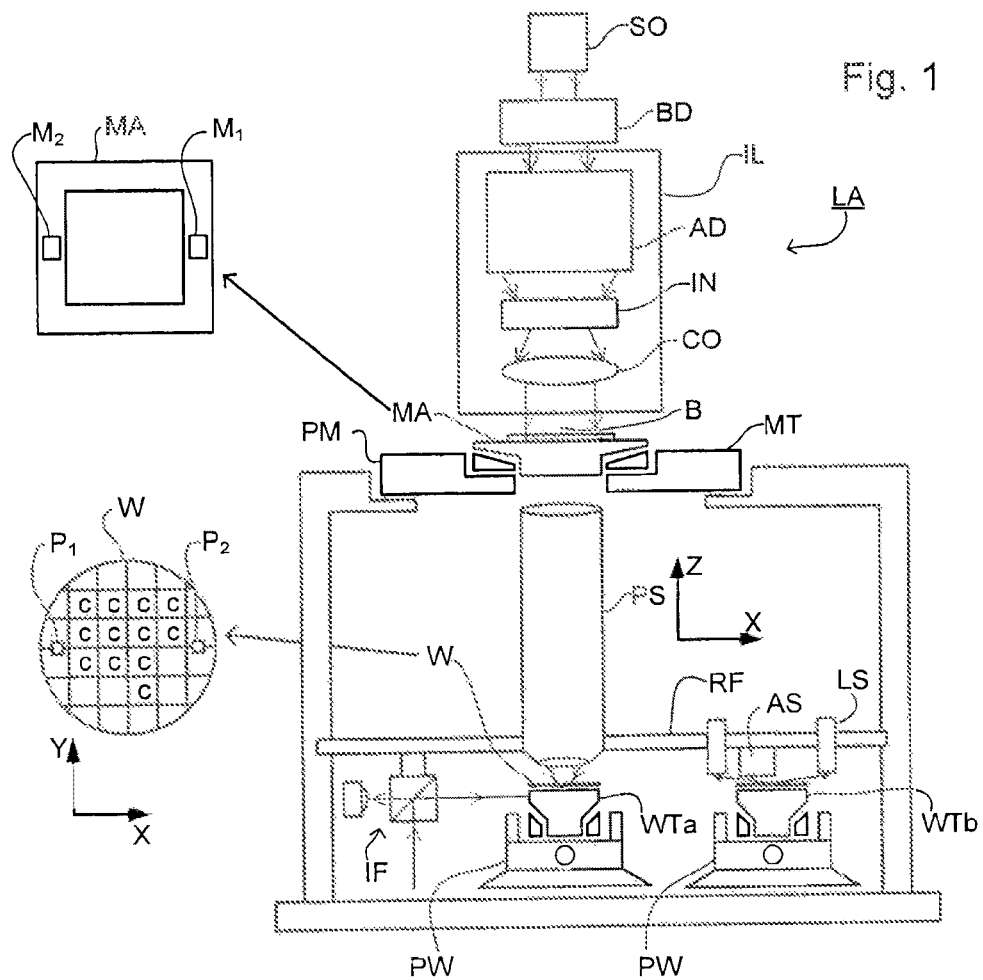
FIG. 1 depicts a lithographic apparatus according to an embodiment of the present invention.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan. In general, movement of the patterning device support (e.g., mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g., mask table) MT may be connected to a short-stroke actuator only, or may be fixed.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. The alignment system, which detects the alignment markers is described further below.

The depicted apparatus could be used in at least one of the following modes:

1. In step mode, the patterning device support (e.g., mask table) MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g., mask table) MT and the substrate table WT are scanned synchronously while a pattern imparted to the radiation beam is projected onto a target portion C (i.e., a single dynamic exposure). The velocity and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g., mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Lithographic apparatus LA is of a so-called dual stage type which has two substrate tables WTa, WTb and two stations—an exposure station and a measurement station—between which the substrate tables can be exchanged. While one substrate on one substrate table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS. This enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations.

Figure 2:
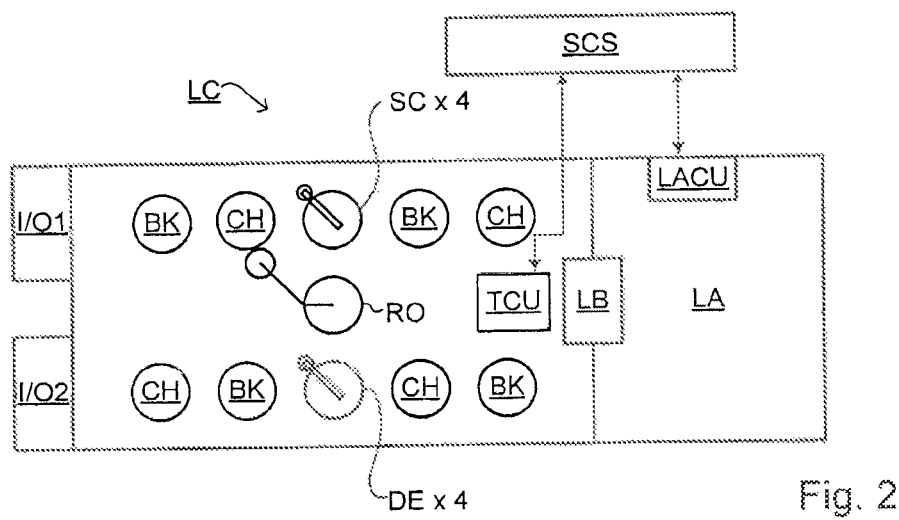
FIG. 2 depicts a lithographic cell or cluster according to an embodiment of the present invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

A dark field metrology apparatus suitable for use in embodiments of the present invention is shown in FIG. 3(a). A target grating T and diffracted rays are illustrated in more detail in FIG. 3(b). The dark field metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 (e.g., a xenon lamp) is directed onto substrate W via a beam splitter 15 by an optical system comprising lenses 12, 14 and objective lens 16. These lenses are arranged in a double sequence of a 4 F arrangement. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

As shown in FIG. 3(b), target grating T is placed with substrate W normal to the optical axis O of objective lens 16. A ray of illumination I impinging on grating T from an angle off the axis O gives rise to a zeroth order ray (solid line 0) and two first order rays (dot-chain line +1 and double dot-chain line −1). It should be remembered that with an overfilled small target grating, these rays are just one of many parallel rays covering the area of the substrate including metrology target grating T and other features. Since the aperture in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches and illumination angles can be designed or adjusted so that the first order rays entering the objective lens are closely aligned with the central optical axis. The rays illustrated in FIGS. 3(a) and 3(b) are shown somewhat off axis, purely to enable them to be more easily distinguished in the diagram.

At least the 0 and +1 orders diffracted by the target on substrate W are collected by objective lens 16 and directed back through beam splitter 15. Returning to FIG. 3(a), both the first and second illumination modes are illustrated, by designating diametrically opposite apertures labeled as north (N) and south (S). When the incident ray I is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A second beam splitter 17 divides the diffracted beams into two measurement branches. In a first measurement branch, optical system 18 forms a diffraction spectrum (pupil plane image) of the target on first sensor 19 (e.g., a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for many measurement purposes such as reconstruction, which are not the subject of the present disclosure.

In the second measurement branch, optical system 20, 22 forms an image of the target on the substrate W on sensor 23 (e.g., a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to image processor and controller PU, the function of which will depend on the particular type of measurements being performed. Note that the term 'image' is used here in a broad sense. An image of the grating lines as such will not be formed, if only one of the −1 and +1 orders is present.

The particular forms of aperture plate 13 and field stop 21 shown in FIG. 3 are purely examples. In another embodiment of the present invention, on-axis illumination of the targets is used and an aperture stop with an off-axis aperture is used to pass substantially only one first order of diffracted light to the sensor. In yet other embodiments, 2nd, 3rd and higher order beams (not shown in FIG. 3) can be used in measurements, instead of or in addition to the first order beams.

In order to make the illumination adaptable to these different types of measurement, the aperture plate 13 may comprise a number of aperture patterns formed around a disc, which rotates to bring a desired pattern into place. Alternatively or in addition, a set of plates 13 could be provided and swapped, to achieve the same effect. A programmable illumination device such as a deformable mirror array or transmissive spatial sight modulator can be used also. Moving mirrors or prisms can be used as another way to adjust the illumination mode.

As just explained in relation to aperture plate 13, the selection of diffraction orders for imaging can alternatively be achieved by altering the field stop 21, or by substituting a field stop having a different pattern, or by replacing the fixed field stop with a programmable spatial light modulator. In that case the illumination side of the measurement optical system can remain constant, while it is the imaging side that has first and second modes. In the present disclosure, therefore, there are effectively three types of measurement method, each with its own advantages and disadvantages. In one method, the illumination mode is changed to measure the different orders. In another method, the imaging mode is changed. In a third method, the illumination and imaging modes remain unchanged, but the target is rotated through 180 degrees. In each case the desired effect is the same, namely to select first and second portions of the non-zero order diffracted radiation which are symmetrically opposite one another in the diffraction spectrum of the target. In principle, the desired selection of orders could be obtained by a combination of changing the illumination modes and the imaging modes simultaneously, but that is likely to bring disadvantages for no advantage, so it will not be discussed further.

While the optical system used for imaging in the present examples has a wide entrance pupil which is restricted by the field stop 21, in other embodiments or applications the entrance pupil size of the imaging system itself may be small enough to restrict to the desired order, and thus serve also as the field stop. Different aperture plates are shown in FIGS. 3(c) and (d) which can be used as described further below.

Typically, a target grating will be aligned with its grating lines running either north-south or east-west. That is to say, a grating will be aligned in the X direction or the Y direction of the substrate W. Note that aperture plate 13N or 13S can only be used to measure gratings oriented in one direction (X or Y depending on the set-up). For measurement of an orthogonal grating, rotation of the target through 90° and 270° might be implemented. More conveniently, however, illumination from east or west is provided in the illumination optics, using the aperture plate 13E or 13W, shown in FIG. 3(c). The aperture plates 13N to 13W can be separately formed and interchanged, or they may be a single aperture plate which can be rotated by 90, 180 or 270 degrees. As mentioned already, the off-axis apertures illustrated in FIG. 3(c) could be provided in field stop 21 instead of in illumination aperture plate 13. In that case, the illumination would be on axis.

FIG. 3(d) shows a third pair of aperture plates that can be used to combine the illumination modes of the first and second pairs. Aperture plate 13NW has apertures at north and east, while aperture plate 13SE has apertures at south and west. Provided that cross-talk between these different diffraction signals is not too great, measurements of both X and Y gratings can be performed without changing the illumination mode.

FIG. 4 depicts a composite target formed on a substrate according to known practice. The composite target comprises four gratings 32 to 35 positioned closely together so that they will all be within a measurement spot 31 formed by the illumination beam of the metrology apparatus. The four targets thus are all simultaneously illuminated and simultaneously imaged on sensors 19 and 23. In an example dedicated to overlay measurement, gratings 32 to 35 are themselves composite gratings formed by overlying gratings that are patterned in different layers of the semi-conductor device formed on substrate W. Gratings 32 to 35 may have differently biased overlay offsets in order to facilitate measurement of overlay between the layers in which the different parts of the composite gratings are formed. Gratings 32 to 35 may also differ in their orientation, as shown, so as to diffract incoming radiation in X and Y directions. In one example, gratings 32 and 34 are X-direction gratings with biases of the +d, −d, respectively. This means that grating 32 has its overlying components arranged so that if they were both printed exactly at their nominal locations one of the components would be offset relative to the other by a distance d. Grating 34 has its components arranged so that if perfectly printed there would be an offset of d but in the opposite direction to the first grating and so on. Gratings 33 and 35 are Y-direction gratings with offsets +d and −d respectively. While four gratings are illustrated, another embodiment might require a larger matrix to obtain the desired accuracy. For example, a 3×3 array of nine composite gratings may have biases −4d, −3d, −2d, −d, 0, +d, +2d, +3d, +4d. Separate images of these gratings can be identified in the image captured by sensor 23.

FIG. 5 shows an example of an image that may be formed on and detected by the sensor 23, using the target of FIG. 4 in the apparatus of FIG. 3, using the aperture plates 13NW or 13SE from FIG. 3(d). While the pupil plane image sensor 19 cannot resolve the different individual gratings 32 to 35, the image sensor 23 can do so. The cross-hatched rectangle represents the field of the image on the sensor, within which the illuminated spot 31 on the substrate is imaged into a corresponding circular area 41. Within this, rectangular areas 42-45 represent the images of the small target gratings 32 to 35. If the gratings are located in product areas, product features may also be visible in the periphery of this image field. Image processor and controller PU processes these images using pattern recognition to identify the separate images 42 to 45 of gratings 32 to 35. In this way, the images do not have to be aligned very precisely at a specific location within the sensor frame, which greatly improves throughput of the measuring apparatus as a whole. However the need for accurate alignment remains if the imaging process is subject to non-uniformities across the image field. In one embodiment of the present invention, four positions P1 to P4 are identified and the gratings are aligned as much as possible with these known positions.

Once the separate images of the gratings have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an important example of such a parameter.

FIG. 6 illustrates how, using for example the method described in application WO 2011/012624, overlay error between the two layers containing the component gratings 32 to 35 is measured through asymmetry of the gratings, as revealed by comparing their intensities in the +1 order and −1 order dark field images. At step S1, the substrate, for example a semiconductor wafer, is processed through the lithographic cell of FIG. 2 one or more times, to create a structure including the overlay targets 32-35. At S2, using the metrology apparatus of FIG. 3, an image of the gratings 32 to 35 is obtained using only one of the first order diffracted beams (say −1). Then, whether by changing the illumination mode, or changing the imaging mode, or by rotating substrate W by 180° in the field of view of the metrology apparatus, a second image of the gratings using the other first order diffracted beam (+1) can be obtained (step S3). Consequently the +1 diffracted radiation is captured in the second image.

Note that, by including only half of the first order diffracted radiation in each image, the 'images' referred to here are not conventional dark field microscopy images. The individual grating lines will not be resolved. Each grating will be represented simply by an area of a certain intensity level. In step S4, a region of interest (ROI) is carefully identified within the image of each component grating, from which intensity levels will be measured. This is done because, particularly around the edges of the individual grating images, intensity values can be highly dependent on process variables such as resist thickness, composition, line shape, as well as edge effects generally.

Having identified the ROI for each individual grating and measured its intensity, the asymmetry of the grating structure, and hence overlay error, can then be determined. This is done by the image processor and controller PU in step S5 comparing the intensity values obtained for +1 and −1 orders for each grating 32-35 to identify any difference in their intensity, and (S6) from knowledge of the overlay biases of the gratings to determine overlay error in the vicinity of the target T.

In the prior applications, mentioned above, various techniques are disclosed for improving the quality of overlay measurements using the basic method mentioned above. For example, the intensity differences between images may be attributable to differences in the optical paths used for the different measurements, and not purely asymmetry in the target. The illumination source 11 may be such that the intensity and/or phase of illumination spot 31 is not uniform. Corrections can the determined and applied to minimize such errors, by reference for example to the position of the target image in the image field of sensor 23.

In a solution proposed in WO 2011/023517, which is incorporated by reference herein in its entirety, the position of the target is used to correct the measured intensity through calibration. For the calibration, a series of measurements at shifted positions is performed to correct future measurements. In these subsequent measurements the position offset of the target with respect to the nominal position is measured, and a correction based on a calibration table is applied.

FIG. 7 shows a graph of overlay measurement error OE (in nm), measured using a known diffraction-based overlay method, versus position X (in nm) of the center of the target measured from center of the illumination spot. Overlay measurement error OE is the difference in the value of measured overlay at the x-position X from the value measured at the center of the illumination spot (X=0). In FIG. 7 the target T is a grating periodic in the x-direction, and X is negative. At the left-hand side of the linear plot the target T is offset by a negative distance from the center of the illumination spot 71, and there is a positive overlay measurement error OE. At the center of the linear plot the target T is centered on the illumination spot 72, and X is zero. At the right-hand side of the linear plot the target T is offset by a positive distance X from the center of the measurement spot 73, and there is a negative overlay measurement error OE with the same magnitude, but opposite sign to that at the left hand side. Thus the plot is linear and passes through the origin.

For such a dependency of overlay on position offset (e.g., with a constant slope), the accuracy of the method disclosed in WO 2011/023517 is limited due to variation of the dependency across the wafer. A calibration performed according to WO 2011/023517 at one location on a wafer would not be useful at another area of the same wafer or on other wafers.

In embodiments of the present invention the approach is to estimate and correct the overlay variation as function of offset for each measurement rather than using a calibration before each wafer or lot. Therefore the effect of the position error in the wafer stage movement, and the resulting non-centered position of the target in the illumination spot, can be compensated for.

Different embodiments include:
(1) Multi-measurement: a. Perform two or more measurements in each direction (x and y) on the target with a fixed position offset between measurements. b. Determine the slope of the overlay variation from the difference in overlay values calculated for each individual measurement. c. Measure the absolute position offset of at least one measurement (e.g., by pattern recognition). d. Determine the true overlay from the absolute position offset and the measured slope.
(2) Multi-target: a. Physically divide each grating of a dark-field diffraction-based overlay target into two or more sub-gratings, as illustrated in FIG. 8c. b. Measure the overlay for each (combination of) sub-gratings individually. c. Determine the slope of the overlay variation from the difference between the results of the two (or more) sub-gratings. d. Measure the absolute position offset of the target (e.g., by pattern recognition). e. Determine the true overlay from the absolute position offset and the measured slope.

(3) Multi-fit: a. Using a normal a dark-field diffraction-based overlay target (with one physical grating per direction and bias), as described with reference to FIGS. 4 and 5. b. Apply a set of multiple (two or more) fit regions across a grating with positive bias, with a known and fixed position offset, as illustrated in FIG. 8d. c. Apply a second set of fit regions across the grating with negative bias, where the relative offset of the fit regions is the same as for the first grating. d. For each pair of fit regions, determine the overlay. e. Determine the slope of the overlay as function of position offset from the set of fits. f. Measure the absolute position offset of the target (e.g., by pattern recognition). g. Determine the true overlay from the absolute position offset and the measured slope.

Multi-fit method (3) may be extended to a continuous fit of the overlay as function of x and y coordinates.

Multi-measurement method (1) may be used when using a pupil sensor for measurement of overlay and also for dark-field diffraction-based overlay measurements, but requires physical movement of the illumination spot relative to the target (for example by moving the stage or scanning the illumination spot) between individual measurements, incurring some throughput penalty. The total sensor integration time is not necessarily increased because the total number of detected photons can be divided over the multiple measurements.

Multi-target method (2) and multi-fit method (3) may be used for dark field overlay measurements.

Figure 8A:
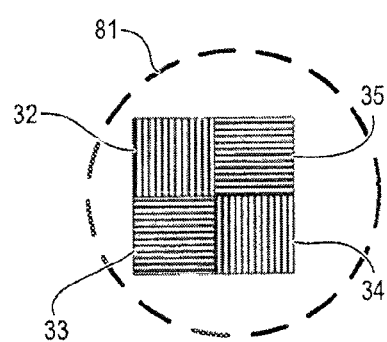
Figure 8B:
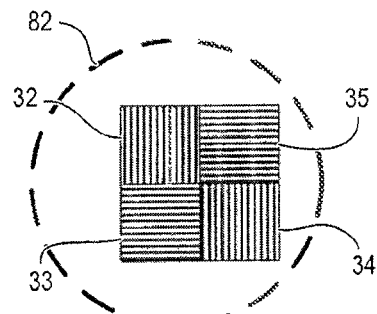
Figure 8C:
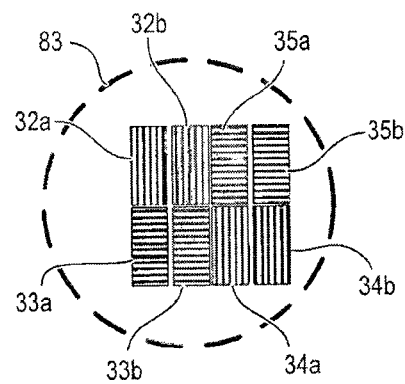
Figure 8D:
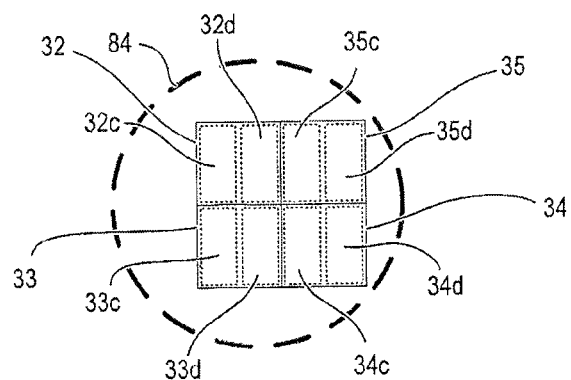

FIGS. 8a to 8d illustrate an illumination spot with a target with multiple gratings in different positions. With reference to FIG. 8a, the target structure 32-35 is formed on the substrate. The target structure includes in this example four periodic structures, gratings 32, 33, 34 and 35. The substrate is illuminated with a beam of radiation having an illumination region, in this case a circular spot, 81 on the substrate with a size larger than each grating to be measured and in this case larger than the entire target. Radiation scattered by each grating is detected in a dark-field scatterometer to obtain a plurality of (two or more) measurement signals at a corresponding plurality of positions across the illumination region (for example by moving the wafer stage or moving the illumination spot) as shown in FIGS. 8a to 8b. In FIG. 8a a measurement is performed when the target is at the left of the illumination spot 81 and another measurement is performed when the target is at the right of the illumination spot 82 in FIG. 8b. It will be appreciated that the two or more measurements may be performed at just one side of the center of the illumination region. The measurement signals, in this case the average intensity value of each region of interest found by pattern matching in the image captured by sensor 23, may be used to calculate overlay at the different positions. The dependence of the property overlay as a function of position in the illumination spot can then be determined. If the dependence is not linear, then instead of slope, other parameters modelling the dependence may be used, e.g., polynomial coefficients.

After measuring the absolute position offset of the identified region of interest, and using the determined dependence (slope in this example) of overlay versus position, then an estimated value of the overlay at the illumination spot's center can be calculated. This calculated (or estimated or corrected) overlay can be used as the determined and reported overlay for the target. Thus a value is calculated of the overlay corresponding to a nominal position of the grating in the illumination spot when the radiation was detected, by using the detected radiation and measurement signals and correcting for variation of the overlay as a function of the grating's position in the illumination spot. The nominal position of the grating in the illumination spot may be where multiple anti-symmetric curves or straight lines, that can arise under different system conditions, cross. In a homogeneous illumination spot the nominal position would be the center, but any non-zero asymmetric intensity component might shift the crossing to another nominal position.

Alternatively, when there is a dependence of the scattering property intensity (in the region of interest) versus position, the dependence of intensity versus position (rather than overlay versus position) can be determined, then an estimated value of the intensity at the illumination spot's center can be calculated for each of the +1st order and −1st order measurements. The calculated (or estimated or corrected)+1st order and −1st order measurements can be used to determine and report the overlay for the target.

Furthermore, when there is a dependence of the scattering property, which is the difference in intensity between the +1st and −1st order measurements, versus position, the dependence of the difference in intensity between the +1st and −1st order measurements versus position (rather than overlay versus position) can be determined, then an estimated value of the difference in intensity between the +1st and −1st order measurements at the illumination spot's center can be calculated. The calculated (or estimated or corrected) value of the difference between the +1st order and −1st order measurements can be used to determine and report the overlay for the target.

With reference to FIG. 8c, a multi-target structure is formed on the substrate as described above for method (2). The target structure includes in this example four periodic structures each split into two sub gratings: 32a and 32b; 33a and 33b; 34a and 34b; and 35a and 35b.

With reference to FIG. 8d, the target structure 32-35 is formed on the substrate. In this example, gratings 32 and 34 are X-direction gratings with biases of the +d, −d, respectively. Gratings 33 and 35 are Y-direction gratings with offsets +d and −d respectively. A set of multiple (two or more) fit regions 32c and 32d (also 33c and 33d) are applied across grating with positive bias 32 (also 33), with a known and fixed position offset. A second set of fit regions 34c and 34d (also 35c and 35d) are applied across the grating with negative bias 34 (also 35), where the relative offset of the fit regions is the same as for the first grating 32 (also 33).

For each pair of fit regions with different biases (e.g., 32c, 34c), the overlay is determined, using $+1^{st}$ order and $-1^{st}$ order measurements. Using the plurality of measurement signals extracted from the fit regions, a value of the target asymmetry at the illumination spot's center is calculated. This is done by calculating the slope of the overlay as function of position offset from the set of fits. The absolute position offset of the target is measured or determined (e.g., by pattern recognition). The overlay at the center of the illumination spot is calculated from the absolute position offset and the measured slope. The calculated value of the target asymmetry is then used as the overlay of the target structure or used to calculate the overlay of the target structure.

FIG. 9 illustrates a flow chart of a method according to an embodiment of the present invention using dark-field diffraction-based overlay.

In step 91 a wafer is processed using a lithography apparatus to produce a target on the wafer.

In step 92, at a plurality of positions across the illumination spot, the $-1^{st}$ order scatterometry image is measured using a first illumination mode and the $+1^{st}$ order scatterometry image is measured using a second illumination mode. These two measurements (for $-1^{st}$ order and $+1^{st}$ order) may be performed before and after moving the relative position of the illumination spot and the target (for example by moving the stage), as shown in FIGS. 8a and 8b. Alternative combinations of movement and measurement can be used, for example measuring the $-1^{st}$ order before and after a first movement, then measuring the $+1^{st}$ order before and after a second movement, however this example is clearly less efficient when using stage movement, but may be practical if the movement is provided by beam scanning. The order of the $+1^{st}$ and $-1^{st}$ orders may be reversed. In other embodiments, corresponding to FIGS. 8c and 8d, no movement of the relative position of the illumination spot and the target is used. Instead the target is either divided into regions at a plurality of positions in the illumination spot (FIG. 8c) or the target extends to a plurality of positions in the illumination spot (FIG. 8d). In either case, regions of interest at a plurality of positions in the illumination spot are used to measure the scatterometry image.

In step 93 the intensity signal is extracted from each recognized region of interest (corresponding to a target grating or region of a target grating) at each position across the illumination spot, for each of the $+1^{st}$ and $-1^{st}$ order scatterometry images.

In step 94 the difference image between the $+1^{st}$ and $-1^{st}$ order signals is calculated for each target grating (or region of a target grating) at each position in order to determine target asymmetry at each position The target asymmetry may be equivalent to overlay, or overlay may be calculated from the target asymmetry for each position.

In step 95, the absolute position offset from the center of the illumination spot of at least one target region of interest is measured, or determined from the image. If not measured directly, the position offset of other regions of interest in the current image (or other images captured while there is no relative movement between the illumination spot and the target, for example if the stage position is fixed), can be determined using this absolute position offset.

In step 96, the slope of target asymmetry versus position is calculated from the target asymmetry at each position (determined in step 94) and measured (or determined) region of interest positions. The order of steps 95 and 96 may be reversed.

In step 97, using the absolute position offset of the region of interest and the slope of target asymmetry (or overlay) versus position, then an estimated value of the target asymmetry (or overlay) at the illumination spot's center can be calculated. This calculated (or estimated or corrected) target asymmetry (or overlay) can be used as the determined and reported overlay for the target.

Alternatively, when there is a linear relationship of intensity versus position (rather than target asymmetry or overlay versus position), the slope of intensity versus position can be determined, then an estimated value of the intensity at the illumination spot's center can be calculated for each of the +1st order and −1st order measurements. The calculated (or estimated or corrected)+1st order and −1st order measurements can be used in the conventional way to determine and report the overlay for the target.

In step 98, if the overlay is not yet calculated, the target asymmetries are used to determine overlay or some other performance parameter.

Although FIG. 9 relates to measuring the overlay in the x-direction, it should be appreciated that the same steps may be used to measure the overlay in the y-direction, or any other chosen direction in the plane of the wafer.

FIG. 10 illustrates a method in accordance with another embodiment of the present invention using a pupil sensor for measurement of overlay. This method is useful when the environment around the grating is empty of features, for example when it is non-reflective. In step 1001 a wafer is processed using lithography apparatus to produce a target on the wafer. In step 1002 the pixels on which the $-1^{st}$ and $+1^{st}$ orders are incident in the pupil plane are measured by sensor 19 at a plurality of x-positions of the target in the illumination spot. In step 1003 the difference between the integrated $-1^{st}$ and $+1^{st}$ order measurement signal thus captured is calculated in order to determine the overlay. In step 1004 the slope of overlay versus x-position is calculated. In step 1005 the absolute position of at least one measurement is determined. In step 1006 the overlay is determined from the absolute position offset and the measured slope.

FIG. 11 shows a graph of overlay measurement error OE (in nm), measured using a known diffraction-based overlay method, versus position X (in nm) of the center of the target measured from center of the illumination spot. Overlay measurement error OE is the difference in the value of measured overlay at the x-position from the value measured at the center of the illumination spot (X=0). In FIG. 11 the target T is a grating periodic in the x-direction. Towards the left-hand side of the curve the target T is offset by a negative distance from the center of the illumination spot 1101, and there is a positive overlay measurement error OE. At the center of the curve the target T is centered on the illumination spot 1102, and OE is zero. Towards the right-hand side of the curve the target T is offset by a positive distance from the center of the measurement spot 1103, and there is a negative overlay measurement error OE with the same magnitude, but opposite sign to that at the left hand side. At the far left-hand side of the curve the target T is offset by a large negative distance from the center of the illumination spot 1104, so that the whole of the target T is outside the measurement spot 1104 and the overlay measurement error OE is not measurable. Similarly, at the far right-hand side of the curve the target T is offset by a large positive distance from the center of the illumination spot 1105, so that the whole of the target T is outside the measurement spot 1105 and the overlay measurement error OE is not measurable. Thus the curve is anti-symmetric.

In embodiments of the present invention the approach is to generate scanning measurement signals (for example by collecting light in a scatterometer pupil plane image sensor 19 or dark-field sensor 23, with reference to FIG. 3a) while scanning either the target fully through the illumination spot, or vice versa. This has the effect of integrating, or equivalently averaging, across the anti-symmetric curve shown in FIG. 11. The anti-symmetric overlay measurement error will therefore be cancelled out by integrating along the path of the target with respect to the illumination spot. Therefore the effect of the position error in the wafer stage movement, and the resulting non-centered position of the target in the illumination spot, is diminished.

With reference to FIGS. 12a to 12c, the target structure 32-35 is formed on the substrate. The target structure includes in this example four periodic structures, gratings 32, 33, 34 and 35. The substrate is illuminated with a beam of radiation having an illumination region, in this case a circular spot, 1201 on the substrate with a size larger than each grating and in this case larger than the entire target. Radiation scattered by each grating is detected in a dark-field scatterometer to obtain measurement signals while the illumination spot 1201-1205 is scanned (for example by moving the wafer stage or moving the illumination spot) as shown in FIGS. 12a to 12c, along a path with the target 32-35 passing fully through the illumination spot 1201-1205. Thus in FIG. 12a the illumination spot 1201 starts at the left of the target, with the target 32-35 (or at least the region of interest of the target, e.g., 32) outside the illumination spot. Then by relative displacement between the target and illumination spot, the illumination spot moves across the target as shown by 1202, 1203 and 1204 in FIG. 12b. The measurement spot 1205 ends the path with the target 32-35 (or at least the region of interest of the target, e.g., 32) outside it, as shown in FIG. 12c. The measurement signals, in this case the average intensity value of each region of interest found by pattern matching in the image captured by sensor 23, are integrated along the path. This integration can be performed for example by capturing multiple frames along the path and then in each frame using pattern recognition to locate each region of interest (if present) corresponding to each grating, then summing or averaging the intensity for each respective region of interest across the frames. As the image of the target moves across the sensor 23 field of view, then known object tracking methods may be used to locate the region of interest for each respective grating, so that the integration can be performed real-time, rather than storing each of the frames along the path. In another example, the known method of time delayed integration (TDI) may be used with image capture on a CCD (charge coupled device) sensor in the sensor 23, synchronized with the movement of the stage relative to the illumination spot in order to keep the region of interest stationary in the image frame and to simplify the identification of the region or regions of interest.

FIG. 13 illustrates a flow chart of a method according to an embodiment of the present invention using dark-field diffraction-based overlay. In step 1301 a wafer is processed using a lithography apparatus to produce a target on the wafer. In step 1302 the −1st order scatterometry image is measured using a first illumination mode while scanning in an x-direction fully through the overfilled illumination spot. In step 1303 the +1st order scatterometry image is measured using a second illumination mode while again scanning in the x-direction fully through the overfilled illumination spot. This second scan through the illumination spot may be performed in the same direction along the x-axis as the scan one or the opposite direction. The order of the +1st and −1st orders may be reversed. In step 1304 the intensity signal is extracted from each recognized region of interest (corresponding to a target grating) along the path through the illumination spot, for each of the +1st and −1st order scatterometry images. At step 1305 the extracted signal is integrated along the path. As mentioned previously this could be performed by for example summing or averaging across frames recorded along the path. In step 1306 the difference image between the +1st and −1st order integrated signals is calculated for each target in order to determine target asymmetry. In an alternative embodiment the +1st order image and −1st order images may be integrated in real time along each scan path and then the integrated image for each of the +1st and −1st orders then compared to calculate a difference between them. In step 1307 the target asymmetries are used to determine overlay or some other performance parameter. Although FIG. 13 relates to measuring the overlay in the x-direction, it should be appreciated that the same steps may be used to measure the overlay in the y-direction, or any other chosen direction on the plane of the wafer. For example, with a compound target having at least two gratings having periodicity in orthogonal directions, for example as shown in FIGS. 4 and 5, the scan can be performed with the relative movement having components in each of the orthogonal directions (such as a diagonal x-y-direction), and a plurality of measurement signals are extracted from separate regions of interest in the single image corresponding to the at least two periodic structures.

FIG. 14 illustrates a method in accordance with another embodiment of the present invention using a pupil sensor for measurement of overlay. This method is useful when the environment around the grating is empty of features, for example when it is non-reflective. In step 1401 a wafer is processed using lithography apparatus to produce a target on the wafer. In step 1402 the pixels on which the −1st and +1st orders are incident in the pupil plane are integrated by sensor 19 while scanning the target in the x-direction fully through the overfilled illumination spot. In step 1403 the difference between the integrated −1st and +1st order measurement signal thus captured is calculated in order to determine the target asymmetry. In step 1404 the target asymmetries are used to determine overlay or some other performance parameter.

FIG. 15a illustrates the passing of a measurement spot 1501 fully across a target 1502 from one side to the other. The environment E around the target is also depicted. FIG. 15b shows the target 1503 being scanned through a stationary measurement spot 1504. Thus it is clear that the two situations produce the same relative displacement. The reference frame of the sensor 23 may be for example the same as the illumination spot, in the case scanning the wafer stage, or the same as the target, in the case of scanning the measurement spot.

While the target structures described above are metrology targets specifically designed and formed for the purposes of measurement, in other embodiments, properties may be measured on targets which are functional parts of devices formed on the substrate. Many devices have regular, grating-like structures. The terms 'target grating' and 'target structure' as used herein do not require that the structure has been provided specifically for the measurement being performed.

In association with the physical grating structures of the targets as realized on substrates and patterning devices, an embodiment may include a computer program containing one or more sequences of machine-readable instructions describing a methods of producing targets on a substrate, measuring targets on a substrate and/or analyzing measurements to obtain information about a lithographic process. This computer program may be executed for example within unit PU in the apparatus of FIG. 3 and/or the control unit LACU of FIG. 2. There may also be provided a data storage medium (e.g., semiconductor memory, magnetic or optical disk) having such a computer program stored therein.

Although specific reference may have been made above to the use of embodiments of the present invention in the context of optical lithography, it will be appreciated that the present invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, Further embodiments according to the invention are provided in below numbered clauses:

1. A method of determining a property of a target comprising at least one periodic structure, the target formed by a lithographic process on a substrate, the method including the steps of:
   (a) illuminating the substrate with a beam of radiation, having an illumination region on the substrate with a size larger than at least one periodic structure of the target;
   (b) detecting radiation scattered by the at least one periodic structure at a plurality of positions in the illumination region; and
   (c) calculating a value of the property of the target corresponding to a nominal position of the at least one periodic structure in the illumination region when the radiation was detected, by using the detected radiation and correcting for variation of the property as a function of the at least one periodic structure's position in the illumination region.
2. The method of clause 1, further including:
   determining a dependence of a scattering property obtained from the detected radiation as a function of position in the illumination region; and
   determining the position offset of at least one of at least one the periodic structure,
   wherein step (c) includes using the determined dependence and the determined position offset.
3. The method of clause 1 or clause 2 wherein in step (b) the radiation is detected with a plurality of discrete displacements of the illumination region relative to the target, the plurality of discrete displacements corresponding to the plurality of positions in the illumination region.
4. The method of clause 1 or clause 2 wherein, the target comprises a plurality of sub-targets, spaced to provide the plurality of positions in the illumination region.
5. The method of clause 1 or clause 2 wherein, in step (b) the radiation is detected at a plurality of regions of interest in an image of the target, the regions of interest corresponding to the plurality of positions in the illumination region.
6. The method of clause 1, wherein: step (b) is performed while at least one of the illumination region and the target are moved relative to each other along a path with the at least one periodic structure passing fully through the illumination region; and the method further includes integrating at least one measurement signal along the path and step (c) includes using the at least one integrated measurement signal.
7. A method according to 6, wherein in step (b) the at least one measurement signal is obtained by forming an image of the at least one periodic structure, the image being formed using a part of non-zero-order diffracted radiation while excluding zero-order diffracted radiation.
8. A method according to clause 7, wherein the target comprises at least two periodic structures having periodicity in orthogonal directions and steps (a) to (b) are repeated with the relative movement in each of the orthogonal directions.
9. A method according to clause 7, wherein the target comprises at least two periodic structures having periodicity in orthogonal directions and steps (a) to (b) are performed with the relative movement having components in each of the orthogonal directions, and a plurality of measurement signals are extracted from separate regions of interest in the single image corresponding to the at least two periodic structures.
10. A method according to clause 6, wherein in step (c) the at least one measurement signal is obtained from an angularly resolved spectrum.
11. A method of determining a property of a target comprising at least one periodic structure, the target formed by a lithographic process on a substrate, the method including the steps of:
    (a) illuminating the substrate with a beam of radiation, having an illumination region on the substrate with a size larger than at least one periodic structure of the target;
    (b) detecting radiation scattered by the at least one periodic structure at a plurality of positions in the illumination region; and
    (c) calculating a value of the property of the target corresponding to a nominal position of the at least one periodic structure in the illumination region when the radiation was detected, by using the detected radiation and correcting for variation of the property as a function of the at least one periodic structure's position in the illumination region;
    (d) determining a dependence of a scattering property obtained from the detected radiation as a function of position in the illumination region; and
    (e) determining the position offset of at least one of the at least one periodic structure,
    wherein step (c) includes using the determined dependence and the determined position offset.
12. The method of clause 11 wherein in step (b) the radiation is detected with a plurality of discrete displacements of the illumination region relative to the target, the plurality of discrete displacements corresponding to the plurality of positions in the illumination region.
13. The method of clause 11 wherein, the target comprises a plurality of sub-targets, spaced to provide the plurality of positions in the illumination region.
14. The method of clause 11 wherein, in step (b) the radiation is detected at a plurality of regions of interest in an image of the target, the regions of interest corresponding to the plurality of positions in the illumination region.
15. A method of determining a property of a target comprising at least one periodic structure, the target formed by a lithographic process on a substrate, the method including the steps of:
    (a) illuminating the substrate with a beam of radiation, having an illumination region on the substrate with a size larger than at least one periodic structure of the target;
    (b) detecting radiation scattered by the at least one periodic structure at a plurality of positions in the illumination region; and
    (c) calculating a value of the property of the target corresponding to a nominal position of the at least one periodic structure in the illumination region when the radiation was detected, by using the detected radiation and correcting for variation of the property as a function of the at least one periodic structure's position in the illumination region,
    (d) wherein: step (b) is performed while at least one of the illumination region and the target are moved relative to each other along a path with the at least one periodic structure passing fully through the illumination region; and the method further includes integrating at least one measurement signal along the path and step (c) includes using the at least one integrated measurement signal.
16. A method according to clause 15, wherein in step (b) the at least one measurement signal is obtained by forming an image of the at least one periodic structure, the image being formed using a part of non-zero-order diffracted radiation while excluding zero-order diffracted radiation.

17. A method according to clause 16, wherein the target comprises at least two periodic structures having periodicity in orthogonal directions and steps (a) to (b) are repeated with the relative movement in each of the orthogonal directions.

18. A method according to clause 16, wherein the target comprises at least two periodic structures having periodicity in orthogonal directions and steps (a) to (b) are performed with the relative movement having components in each of the orthogonal directions, and a plurality of measurement signals are extracted from separate regions of interest in the single image corresponding to the at least two periodic structures.

19. A method according to clause 15, wherein in step (c) the at least one measurement signal is obtained from an angularly resolved spectrum.

20. An inspection apparatus configured for determining a property of a target comprising at least one periodic structure, the target formed by a lithographic process on a substrate, the inspection apparatus comprising:
   (a) an illumination arrangement operable to illuminate the substrate with a beam of radiation, having an illumination region on the substrate with a size larger than at least one periodic structure of the target;
   (b) a detection arrangement operable to detect radiation scattered by the at least one periodic structure at a plurality of positions in the illumination region; and
   (c) a computational arrangement operable to calculate a value of the property of the target corresponding to a nominal position of the at least one periodic structure in the illumination region when the radiation was detected, by using the detected radiation and correcting for variation of the property as a function of the at least one periodic structure's position in the illumination region.

21. The inspection apparatus of clause 20, wherein the computational apparatus is further operable to:
   determine a dependence of a scattering property obtained from the detected radiation as a function of position in the illumination region; and
   determine the position offset of at least one of at least one the periodic structure,
   wherein step (c) includes using the determined dependence and the determined position offset.

22. The inspection apparatus of clause 20 or clause 21 wherein the detection arrangement is further operable to detect the radiation with a plurality of discrete displacements of the illumination region relative to the target, the plurality of discrete displacements corresponding to the plurality of positions in the illumination region.

23. The inspection apparatus of clause 20 or clause 21 wherein, the target comprises a plurality of sub-targets, spaced to provide the plurality of positions in the illumination region.

24. The inspection apparatus of clause 20 or clause 21 wherein, the detection arrangement is further operable to detect the radiation at a plurality of regions of interest in an image of the target, the regions of interest corresponding to the plurality of positions in the illumination region.

25. The inspection apparatus of clause 20, further comprising a movement arrangement operable to move at least one of the illumination region and the target relative to each other, and wherein: the detection arrangement is further operable to detect radiation while at least one of the illumination region and the target are moved relative to each other along a path with the at least one periodic structure passing fully through the illumination region; and the computational arrangement is further operable to integrate at least one measurement signal along the path and to calculate the value of the property of the target using the at least one integrated measurement signal.

26. An inspection apparatus according to clause 25, wherein the detection arrangement is further operable to obtain the at least one measurement signal by forming an image of the at least one periodic structure, the image being formed using a part of non-zero-order diffracted radiation while excluding zero-order diffracted radiation.

27. An inspection apparatus according to clause 26, wherein the target comprises at least two periodic structures having periodicity in orthogonal directions and the illumination arrangement and detection arrangement are operable to repeat the respective illumination and detection with the relative movement in each of the orthogonal directions.

28. An inspection apparatus according to clause 26, wherein the target comprises at least two periodic structures having periodicity in orthogonal directions and the illumination arrangement and detection arrangement are operable to perform the respective illumination and detection with the relative movement having components in each of the orthogonal directions, and the computational arrangement is operable to extract a plurality of measurement signals from separate regions of interest in the single image corresponding to the at least two periodic structures.

29. An inspection apparatus according to clause 25, wherein the computational arrangement is operable to obtain the at least one measurement signal from an angularly resolved spectrum.

30. An inspection apparatus configured for determining a property of a target comprising at least one periodic structure, the target formed by a lithographic process on a substrate, the inspection apparatus comprising:
   (a) an illumination arrangement operable to illuminate the substrate with a beam of radiation, having an illumination region on the substrate with a size larger than at least one periodic structure of the target;
   (b) a detection arrangement operable to detect radiation scattered by the at least one periodic structure at a plurality of positions in the illumination region; and
   (c) a computational arrangement operable to:
   (d) determine a dependence of a scattering property obtained from the detected radiation as a function of position in the illumination region;
   determine the position offset of at least one of at least one the periodic structure; and calculate a value of the property of the target corresponding to a nominal position of the at least one periodic structure in the illumination region when the radiation was detected, by using the detected radiation and correcting for variation of the property as a function of the at least one periodic structure's position in the illumination region using the determined dependence and the determined position offset.

31. The inspection apparatus of clause 30 wherein the detection arrangement is further operable to detect the radiation with a plurality of discrete displacements of the illumination region relative to the target, the plurality of discrete displacements corresponding to the plurality of positions in the illumination region.

32. The inspection apparatus of clause 30 wherein, the target comprises a plurality of sub-targets, spaced to provide the plurality of positions in the illumination region.

33. The inspection apparatus of clause 30 wherein, the detection arrangement is further operable to detect the radiation at a plurality of regions of interest in an image of the target, the regions of interest corresponding to the plurality of positions in the illumination region.

34. An inspection apparatus configured for determining a property of a target comprising at least one periodic structure, the target formed by a lithographic process on a substrate, the inspection apparatus comprising:
   (a) an illumination arrangement operable to illuminate the substrate with a beam of radiation, having an illumination region on the substrate with a size larger than at least one periodic structure of the target;
   (b) a detection arrangement operable to detect radiation scattered by the at least one periodic structure at a plurality of positions in the illumination region; and
   (c) a computational arrangement operable to calculate a value of the property of the target corresponding to a nominal position of the at least one periodic structure in the illumination region when the radiation was detected, by using the detected radiation and correcting for variation of the property as a function of the at least one periodic structure's position in the illumination region.
   (d) a movement arrangement operable to move at least one of the illumination region and the target relative to each other, and
   wherein: the detection arrangement is further operable to detect radiation while at least one of the illumination region and the target are moved relative to each other along a path with the at least one periodic structure passing fully through the illumination region; and the computational arrangement is further operable to integrate at least one measurement signal along the path and to calculate the value of the property of the target using the at least one integrated measurement signal.

35. An inspection apparatus according to clause 34, wherein the detection arrangement is further operable to obtain the at least one measurement signal by forming an image of the at least one periodic structure, the image being formed using a part of non-zero-order diffracted radiation while excluding zero-order diffracted radiation.

36. An inspection apparatus according to clause 35, wherein the target comprises at least two periodic structures having periodicity in orthogonal directions and the illumination arrangement and detection arrangement are operable to repeat the respective illumination and detection with the relative movement in each of the orthogonal directions.

37. An inspection apparatus according to clause 35, wherein the target comprises at least two periodic structures having periodicity in orthogonal directions and the illumination arrangement and detection arrangement are operable to perform the respective illumination and detection with the relative movement having components in each of the orthogonal directions, and the computational arrangement is operable to extract a plurality of measurement signals from separate regions of interest in the single image corresponding to the at least two periodic structures.

38. An inspection apparatus according to clause 34, wherein the computational arrangement is operable to obtain the at least one measurement signal from an angularly resolved spectrum.

39. A lithographic system comprising:
   a lithographic apparatus comprising:
      an illumination optical system arranged to illuminate a pattern;
      a projection optical system arranged to project an image of the pattern onto a substrate; and
   an inspection apparatus according to any of clauses 20 to 29, or 30 to 33, or 34 to 38,
   wherein the lithographic apparatus is arranged to use the determined property from the inspection apparatus in applying the pattern to further substrates.

40. A method of manufacturing devices wherein a device pattern is applied to a series of substrates using a lithographic process, the method including inspecting at least one target comprising at least one periodic structure formed as part of or beside the device pattern on at least one of the substrates using an inspection method according to any of clauses 1 to 9, or 10 to 14, or 15 to 19, and controlling the lithographic process for later substrates in accordance with the result of the inspection method.

41. A method comprising:
   illuminating a substrate with a beam of radiation, having an illumination region on the substrate with a size larger than at least one periodic structure of a target on the substrate;
   detecting radiation scattered by the at least one periodic structure at a plurality of positions in the illumination region; and
   calculating a value of the property of the target corresponding to a nominal position of the at least one periodic structure in the illumination region when the radiation was detected, by using the detected radiation and correcting for variation of the property as a function of the at least one periodic structure's position in the illumination region.

42. The method of clause 41, further including:
   determining a dependence of a scattering property obtained from the detected radiation as a function of position in the illumination region; and
   determining the position offset of at least one of at least one the periodic structure,
   the calculating includes using the determined dependence and the determined position offset.

43. The method of clause 41, wherein the detecting detects the radiation is detected with a plurality of discrete displacements of the illumination region relative to the target, the plurality of discrete displacements corresponding to the plurality of positions in the illumination region.

44. The method of clause 41, wherein, the target comprises a plurality of sub-targets, spaced to provide the plurality of positions in the illumination region.

45. The method of clause 41, wherein the detecting detects the radiation is detected at a plurality of regions of interest in an image of the target, the regions of interest corresponding to the plurality of positions in the illumination region.

46. The method of clause 41, wherein:
   the detecting is performed while at least one of the illumination region and the target are moved relative to each other along a path with the at least one periodic structure passing fully through the illumination region;
   the method further includes integrating at least one measurement signal along the path; and
   the calculating includes using the at least one integrated measurement signal.

47. The method of clause 46, wherein:
   the detecting the at least one measurement signal is obtained by forming an image of the at least one periodic structure, the image being formed using a part of non-zero-order diffracted radiation while excluding zero-order diffracted radiation.

48. The method of clause 47, wherein:
   the target comprises at least two periodic structures having periodicity in orthogonal directions the illuminating; and the detecting are repeated with the relative movement in each of the orthogonal directions.

49. The method of clause 47, wherein:
the target comprises at least two periodic structures having periodicity in orthogonal directions;
the illuminating and the detecting are performed with the relative movement having components in each of the orthogonal directions, and
a plurality of measurement signals are extracted from separate regions of interest in the single image corresponding to the at least two periodic structures.

50. The method of clause 46, wherein the calculating the at least one measurement signal is obtained from an angularly resolved spectrum.

51. A method comprising:
illuminating a substrate with a beam of radiation, having an illumination region on the substrate with a size larger than at least one periodic structure of a target on the substrate;
detecting radiation scattered by the at least one periodic structure at a plurality of positions in the illumination region; and
calculating a value of the property of the target corresponding to a nominal position of the at least one periodic structure in the illumination region when the radiation was detected, by using the detected radiation and correcting for variation of the property as a function of the at least one periodic structure's position in the illumination region;
determining a dependence of a scattering property obtained from the detected radiation as a function of position in the illumination region; and
determining the position offset of at least one of the at least one periodic structure,
wherein the calculating includes using the determined dependence and the determined position offset.

52. The method of clause 51, wherein the detecting detects the radiation with a plurality of discrete displacements of the illumination region relative to the target, the plurality of discrete displacements corresponding to the plurality of positions in the illumination region.

53. The method of clause 51, wherein, the target comprises a plurality of sub-targets, spaced to provide the plurality of positions in the illumination region.

54. The method of clause 51, wherein, the detecting detects the radiation at a plurality of regions of interest in an image of the target, the regions of interest corresponding to the plurality of positions in the illumination region.

55. A method comprising:
illuminating a substrate with a beam of radiation, having an illumination region on the substrate with a size larger than at least one periodic structure of a target on the substrate;
detecting radiation scattered by the at least one periodic structure at a plurality of positions in the illumination region; and
calculating a value of the property of the target corresponding to a nominal position of the at least one periodic structure in the illumination region when the radiation was detected, by using the detected radiation and correcting for variation of the property as a function of the at least one periodic structure's position in the illumination region,
wherein the detecting is performed while at least one of the illumination region and the target are moved relative to each other along a path with the at least one periodic structure passing fully through the illumination region; and
the method further includes integrating at least one measurement signal along the path and step (c) includes using the at least one integrated measurement signal.

56. The method of clause 55, wherein the detecting the at least one measurement signal is obtained by forming an image of the at least one periodic structure, the image being formed using a part of non-zero-order diffracted radiation while excluding zero-order diffracted radiation.

57. The method of clause 56, wherein:
the target comprises at least two periodic structures having periodicity in orthogonal directions; and
the illuminating and the detecting are repeated with the relative movement in each of the orthogonal directions.

58. The method of clause 56, wherein:
the target comprises at least two periodic structures having periodicity in orthogonal directions;
the illuminating and the detecting are performed with the relative movement having components in each of the orthogonal directions; and
a plurality of measurement signals are extracted from separate regions of interest in the single image corresponding to the at least two periodic structures.

59. The method of clause 55, wherein in the calculating the at least one measurement signal is obtained from an angularly resolved spectrum.

60. An inspection apparatus comprising:
an illumination arrangement configured to illuminate a substrate with a beam of radiation, having an illumination region on the substrate with a size larger than at least one periodic structure of a target on the substrate;
a detection arrangement configured to detect radiation scattered by the at least one periodic structure at a plurality of positions in the illumination region; and
a computational arrangement configured to calculate a value of the property of the target corresponding to a nominal position of the at least one periodic structure in the illumination region when the radiation was detected, by using the detected radiation and correcting for variation of the property as a function of the at least one periodic structure's position in the illumination region.

61. The inspection apparatus of clause 60, wherein the computational apparatus is further operable to:
determine a dependence of a scattering property obtained from the detected radiation as a function of position in the illumination region; and
determine the position offset of at least one of at least one the periodic structure,
wherein the calculating includes using the determined dependence and the determined position offset.

62. The inspection apparatus of clause 60, wherein the detection arrangement is further operable to detect the radiation with a plurality of discrete displacements of the illumination region relative to the target, the plurality of discrete displacements corresponding to the plurality of positions in the illumination region.

63. The inspection apparatus of clause 60, wherein the target comprises a plurality of sub-targets, spaced to provide the plurality of positions in the illumination region.

64. The inspection apparatus of clause 60, wherein the detection arrangement is further operable to detect the radiation at a plurality of regions of interest in an image of the target, the regions of interest corresponding to the plurality of positions in the illumination region.

65. The inspection apparatus of clause 60, further comprising:
a movement arrangement operable to move at least one of the illumination region and the target relative to each other;
wherein the detection arrangement is further operable to detect radiation while at least one of the illumination region and the target are moved relative to each other along a path with the at least one periodic structure passing fully through the illumination region; and
the computational arrangement is further operable to integrate at least one measurement signal along the path and to calculate the value of the property of the target using the at least one integrated measurement signal.

66. The inspection apparatus of clause 65, wherein the detection arrangement is further operable to obtain the at least one measurement signal by forming an image of the at least one periodic structure, the image being formed using a part of non-zero-order diffracted radiation while excluding zero-order diffracted radiation.

67. The inspection apparatus of clause 66, wherein the target comprises at least two periodic structures having periodicity in orthogonal directions and the illumination arrangement and detection arrangement are operable to repeat the respective illumination and detection with the relative movement in each of the orthogonal directions.

68. The inspection apparatus of clause 66, wherein the target comprises at least two periodic structures having periodicity in orthogonal directions and the illumination arrangement and detection arrangement are operable to perform the respective illumination and detection with the relative movement having components in each of the orthogonal directions, and the computational arrangement is operable to extract a plurality of measurement signals from separate regions of interest in the single image corresponding to the at least two periodic structures.

69. The inspection apparatus of clause 65, wherein the computational arrangement is operable to obtain the at least one measurement signal from an angularly resolved spectrum.

70. An inspection apparatus comprising:
an illumination arrangement operable to illuminate a substrate with a beam of radiation, having an illumination region on the substrate with a size larger than at least one periodic structure of a target on the substrate;
a detection arrangement operable to detect radiation scattered by the at least one periodic structure at a plurality of positions in the illumination region; and
a computational arrangement operable to:
determine a dependence of a scattering property obtained from the detected radiation as a function of position in the illumination region;
determine the position offset of at least one of at least one the periodic structure; and
calculate a value of the property of the target corresponding to a nominal position of the at least one periodic structure in the illumination region when the radiation was detected, by using the detected radiation and correcting for variation of the property as a function of the at least one periodic structure's position in the illumination region using the determined dependence and the determined position offset.

71. The inspection apparatus of clause 70, wherein the detection arrangement is further operable to detect the radiation with a plurality of discrete displacements of the illumination region relative to the target, the plurality of discrete displacements corresponding to the plurality of positions in the illumination region.

72. The inspection apparatus of clause 70, wherein the target comprises a plurality of sub-targets, spaced to provide the plurality of positions in the illumination region.

73. The inspection apparatus of clause 70, the detection arrangement is further operable to detect the radiation at a plurality of regions of interest in an image of the target, the regions of interest corresponding to the plurality of positions in the illumination region.

74. An inspection apparatus comprising:
an illumination arrangement operable to illuminate a substrate with a beam of radiation, having an illumination region on the substrate with a size larger than at least one periodic structure of a target on the substrate;
a detection arrangement operable to detect radiation scattered by the at least one periodic structure at a plurality of positions in the illumination region;
a computational arrangement operable to calculate a value of the property of the target corresponding to a nominal position of the at least one periodic structure in the illumination region when the radiation was detected, by using the detected radiation and correcting for variation of the property as a function of the at least one periodic structure's position in the illumination region; and a movement arrangement operable to move at least one of the illumination
region and the target relative to each other,
wherein: the detection arrangement is further operable to detect radiation while at least one of the illumination region and the target are moved relative to each other along a path with the at least one periodic structure passing fully through the illumination region; and the computational arrangement is further operable to integrate at least one measurement signal along the path and to calculate the value of the property of the target using the at least one integrated measurement signal.

75. The inspection apparatus according to clause 74, wherein the detection arrangement is further operable to obtain the at least one measurement signal by forming an image of the at least one periodic structure, the image being formed using a part of non-zero-order diffracted radiation while excluding zero-order diffracted radiation.

76. The inspection apparatus according to clause 75, wherein the target comprises at least two periodic structures having periodicity in orthogonal directions and the illumination arrangement and detection arrangement are operable to repeat the respective illumination and detection with the relative movement in each of the orthogonal directions.

77. The inspection apparatus according to clause 75, wherein the target comprises at least two periodic structures having periodicity in orthogonal directions and the illumination arrangement and detection arrangement are operable to perform the respective illumination and detection with the relative movement having components in each of the orthogonal directions, and the computational arrangement is operable to extract a plurality of measurement signals from separate regions of interest in the single image corresponding to the at least two periodic structures.

78. The inspection apparatus according to clause 74, wherein the computational arrangement is operable to obtain the at least one measurement signal from an angularly resolved spectrum.

79. A lithographic system comprising:
a lithographic apparatus comprising:
an illumination optical system arranged to illuminate a pattern;
a projection optical system arranged to project an image of the pattern onto a substrate; and an inspection apparatus comprising,
   an illumination arrangement configured to illuminate a substrate with a beam of radiation, having an illumination region on the substrate with a size larger than at least one periodic structure of a target on the substrate;
   a detection arrangement configured to detect radiation scattered by the at least one periodic structure at a plurality of positions in the illumination region; and
   a computational arrangement configured to calculate a value of the property of the target corresponding to a nominal position of the at least one periodic structure in the illumination region when the radiation was detected, by using the detected radiation and correcting for variation of the property as a function of the at least one periodic structure's position in the illumination region,
   wherein the lithographic apparatus is arranged to use the determined property from the inspection apparatus in applying the pattern to further substrates.

80. A method of manufacturing devices wherein a device pattern is applied to a series of substrates using a lithographic process, the method including inspecting at least one target comprising at least one periodic structure formed as part of or beside the device pattern on at least one of the substrates using an inspection method comprising:
   illuminating a substrate with a beam of radiation, having an illumination region on the substrate with a size larger than at least one periodic structure of a target on the substrate;
   detecting radiation scattered by the at least one periodic structure at a plurality of positions in the illumination region; and
   calculating a value of the property of the target corresponding to a nominal position of the at least one periodic structure in the illumination region when the radiation was detected, by using the detected radiation and correcting for variation of the property as a function of the at least one periodic structure's position in the illumination region, and
   controlling the lithographic process for later substrates in accordance with the result of the inspection method.

The foregoing description of the specific embodiments will so fully reveal the general nature of the present invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of determining a property of a target comprising at least one periodic structure, the target formed by a lithographic process on a substrate, the method comprising:
   illuminating the substrate with a beam of radiation, having an illumination region on the substrate with a size larger than at least one periodic structure of the target;
   detecting radiation scattered by the at least one periodic structure at a plurality of positions in the illumination region; and
   calculating a value of the property of the target corresponding to a nominal position of the at least one periodic structure in the illumination region when the radiation was detected, by using the detected radiation and correcting for variation of the property as a function of the at least one periodic structure's position in the illumination region.

2. A method of determining a property of a target comprising at least one periodic structure, the target formed by a lithographic process on a substrate, the method comprising:
   illuminating the substrate with a beam of radiation, having an illumination region on the substrate with a size larger than at least one periodic structure of the target;
   detecting radiation scattered by the at least one periodic structure at a plurality of positions in the illumination region; and
   calculating a value of the property of the target corresponding to a nominal position of the at least one periodic structure in the illumination region when the radiation was detected, by using the detected radiation and correcting for variation of the property as a function of the at least one periodic structure's position in the illumination region;
   determining a dependence of a scattering property obtained from the detected radiation as a function of position in the illumination region; and
   determining the position offset of at least one of the at least one periodic structure, wherein the calculating includes using the determined dependence and the determined position offset.

3. A method of determining a property of a target comprising at least one periodic structure, the target formed by a lithographic process on a substrate, the method comprising:
- illuminating the substrate with a beam of radiation, having an illumination region on the substrate with a size larger than at least one periodic structure of the target;
- detecting radiation scattered by the at least one periodic structure at a plurality of positions in the illumination region; and
- calculating a value of the property of the target corresponding to a nominal position of the at least one periodic structure in the illumination region when the radiation was detected, by using the detected radiation and correcting for variation of the property as a function of the at least one periodic structure's position in the illumination region,
- wherein the detecting is performed while at least one of the illumination region and the target are moved relative to each other along a path with the at least one periodic structure passing fully through the illumination region; and
- integrating at least one measurement signal along the path, wherein the calculating includes using the at least one integrated measurement signal.

4. An inspection apparatus configured for determining a property of a target comprising at least one periodic structure, the target formed by a lithographic process on a substrate, the inspection apparatus comprising:
- an illumination arrangement operable to illuminate the substrate with a beam of radiation, having an illumination region on the substrate with a size larger than at least one periodic structure of the target;
- a detection arrangement operable to detect radiation scattered by the at least one periodic structure at a plurality of positions in the illumination region; and
- a computational arrangement operable to calculate a value of the property of the target corresponding to a nominal position of the at least one periodic structure in the illumination region when the radiation was detected, by using the detected radiation and correcting for variation of the property as a function of the at least one periodic structure's position in the illumination region.

5. An inspection apparatus configured for determining a property of a target comprising at least one periodic structure, the target formed by a lithographic process on a substrate, the inspection apparatus comprising:
- an illumination arrangement operable to illuminate the substrate with a beam of radiation, having an illumination region on the substrate with a size larger than at least one periodic structure of the target;
- a detection arrangement operable to detect radiation scattered by the at least one periodic structure at a plurality of positions in the illumination region; and
- a computational arrangement operable to:
- determine a dependence of a scattering property obtained from the detected radiation as a function of position in the illumination region;
- determine the position offset of at least one of at least one the periodic structure; and
- calculate a value of the property of the target corresponding to a nominal position of the at least one periodic structure in the illumination region when the radiation was detected, by using the detected radiation and correcting for variation of the property as a function of the at least one periodic structure's position in the illumination region using the determined dependence and the determined position offset.

6. An inspection apparatus configured for determining a property of a target comprising at least one periodic structure, the target formed by a lithographic process on a substrate, the inspection apparatus comprising:
- an illumination arrangement operable to illuminate the substrate with a beam of radiation, having an illumination region on the substrate with a size larger than at least one periodic structure of the target;
- a detection arrangement operable to detect radiation scattered by the at least one periodic structure at a plurality of positions in the illumination region; and
- a computational arrangement operable to calculate a value of the property of the target corresponding to a nominal position of the at least one periodic structure in the illumination region when the radiation was detected, by using the detected radiation and correcting for variation of the property as a function of the at least one periodic structure's position in the illumination region;
- a movement arrangement operable to move at least one of the illumination region and the target relative to each other, and
- wherein the detection arrangement is further operable to detect radiation while at least one of the illumination region and the target are moved relative to each other along a path with the at least one periodic structure passing fully through the illumination region; and
- wherein the computational arrangement is further operable to integrate at least one measurement signal along the path and to calculate the value of the property of the target using the at least one integrated measurement signal.

7. A lithographic system comprising:
- a lithographic apparatus comprising:
- an illumination optical system arranged to illuminate a pattern;
- a projection optical system arranged to project an image of the pattern onto a substrate; and
- an inspection apparatus configured for determining a property of a target comprising at least one periodic structure, the target formed by a lithographic process on a substrate, the inspection apparatus comprising:
- an illumination arrangement operable to illuminate the substrate with a beam of radiation, having an illumination region on the substrate with a size larger than at least one periodic structure of the target;
- a detection arrangement operable to detect radiation scattered by the at least one periodic structure at a plurality of positions in the illumination region; and
- a computational arrangement operable to calculate a value of the property of the target corresponding to a nominal position of the at least one periodic structure in the illumination region when the radiation was detected, by using the detected radiation and correcting for variation of the property as a function of the at least one periodic structure's position in the illumination region,
- wherein the lithographic apparatus is arranged to use the determined property from the inspection apparatus in applying the pattern to further substrates.

8. A method of manufacturing devices wherein a device pattern is applied to a series of substrates using a lithographic process, the method comprising:

inspecting at least one target comprising at least one periodic structure formed as part of or beside the device pattern on at least one of the substrates, the inspecting comprises:
  illuminating the substrate with a beam of radiation, having an illumination region on the substrate with a size larger than at least one periodic structure of the target;
  detecting radiation scattered by the at least one periodic structure at a plurality of positions in the illumination region; and
calculating a value of the property of the target corresponding to a nominal position of the at least one periodic structure in the illumination region when the radiation was detected, by using the detected radiation and correcting for variation of the property as a function of the at least one periodic structure's position in the illumination region; and
controlling the lithographic process for later substrates in accordance with the result of the inspection method.

9. A method comprising:
illuminating a substrate with a beam of radiation, having an illumination region on the substrate with a size larger than at least one periodic structure of a target on the substrate;
detecting radiation scattered by the at least one periodic structure at a plurality of positions in the illumination region; and
calculating a value of the property of the target corresponding to a nominal position of the at least one periodic structure in the illumination region when the radiation was detected, by using the detected radiation and correcting for variation of the property as a function of the at least one periodic structure's position in the illumination region.

10. A method comprising:
illuminating a substrate with a beam of radiation, having an illumination region on the substrate with a size larger than at least one periodic structure of a target on the substrate;
detecting radiation scattered by the at least one periodic structure at a plurality of positions in the illumination region; and
calculating a value of the property of the target corresponding to a nominal position of the at least one periodic structure in the illumination region when the radiation was detected, by using the detected radiation and correcting for variation of the property as a function of the at least one periodic structure's position in the illumination region;
determining a dependence of a scattering property obtained from the detected radiation as a function of position in the illumination region; and
determining the position offset of at least one of the at least one periodic structure,
wherein the calculating includes using the determined dependence and the determined position offset.

11. A method comprising:
illuminating a substrate with a beam of radiation, having an illumination region on the substrate with a size larger than at least one periodic structure of a target on the substrate;
detecting radiation scattered by the at least one periodic structure at a plurality of positions in the illumination region; and
calculating a value of the property of the target corresponding to a nominal position of the at least one periodic structure in the illumination region when the radiation was detected, by using the detected radiation and correcting for variation of the property as a function of the at least one periodic structure's position in the illumination region,
wherein the detecting is performed while at least one of the illumination region and the target are moved relative to each other along a path with the at least one periodic structure passing fully through the illumination region;
integrating at least one measurement signal along the path, and
wherein the calculation includes using the at least one integrated measurement signal.

12. An inspection apparatus comprising:
an illumination arrangement configured to illuminate a substrate with a beam of radiation, having an illumination region on the substrate with a size larger than at least one periodic structure of a target on the substrate;
a detection arrangement configured to detect radiation scattered by the at least one periodic structure at a plurality of positions in the illumination region; and
a computational arrangement configured to calculate a value of the property of the target corresponding to a nominal position of the at least one periodic structure in the illumination region when the radiation was detected, by using the detected radiation and correcting for variation of the property as a function of the at least one periodic structure's position in the illumination region.

13. An inspection apparatus comprising:
an illumination arrangement operable to illuminate a substrate with a beam of radiation, having an illumination region on the substrate with a size larger than at least one periodic structure of a target on the substrate;
a detection arrangement operable to detect radiation scattered by the at least one periodic structure at a plurality of positions in the illumination region; and
a computational arrangement operable to:
determine a dependence of a scattering property obtained from the detected radiation as a function of position in the illumination region;
determine the position offset of at least one of at least one the periodic structure; and
calculate a value of the property of the target corresponding to a nominal position of the at least one periodic structure in the illumination region when the radiation was detected, by using the detected radiation and correcting for variation of the property as a function of the at least one periodic structure's position in the illumination region using the determined dependence and the determined position offset.

14. An inspection apparatus comprising:
an illumination arrangement operable to illuminate a substrate with a beam of radiation, having an illumination region on the substrate with a size larger than at least one periodic structure of a target on the substrate;
a detection arrangement operable to detect radiation scattered by the at least one periodic structure at a plurality of positions in the illumination region;
a computational arrangement operable to calculate a value of the property of the target corresponding to a nominal position of the at least one periodic structure in the illumination region when the radiation was detected, by using the detected radiation and correcting for variation of the property as a function of the at least one periodic structure's position in the illumination region; and
a movement arrangement operable to move at least one of the illumination region and the target relative to each other, wherein: the detection arrangement is further operable to detect radiation while at least one of the illumination region and the target are moved relative to each other along a path with the at least one periodic structure passing fully through the illumination region;

and the computational arrangement is further operable to integrate at least one measurement signal along the path and to calculate the value of the property of the target using the at least one integrated measurement signal.

15. A lithographic system comprising:

a lithographic apparatus comprising:

an illumination optical system arranged to illuminate a pattern;

a projection optical system arranged to project an image of the pattern onto a substrate; and an inspection apparatus comprising, an illumination arrangement configured to illuminate a substrate with a beam of radiation, having an illumination region on the substrate with a size larger than at least one periodic structure of a target on the substrate;

a detection arrangement configured to detect radiation scattered by the at least one periodic structure at a plurality of positions in the illumination region; and a computational arrangement configured to calculate a value of the property of the target corresponding to a nominal position of the at least one periodic structure in the illumination region when the radiation was detected, by using the detected radiation and correcting for variation of the property as a function of the at least one periodic structure's position in the illumination region, wherein the lithographic apparatus is arranged to use the determined property from the inspection apparatus in applying the pattern to further substrates.

16. A method of manufacturing devices wherein a device pattern is applied to a series of substrates using a lithographic process, the method including inspecting at least one target comprising at least one periodic structure formed as part of or beside the device pattern on at least one of the substrates using an inspection method comprising:

illuminating a substrate with a beam of radiation, having an illumination region on the substrate with a size larger than at least one periodic structure of a target on the substrate;

detecting radiation scattered by the at least one periodic structure at a plurality of positions in the illumination region; and calculating a value of the property of the target corresponding to a nominal position of the at least one periodic structure in the illumination region when the radiation was detected, by using the detected radiation and correcting for variation of the property as a function of the at least one periodic structure's position in the illumination region, and controlling the lithographic process for later substrates in accordance with the result of the inspection method.

* * * * *